(12) United States Patent
Penna et al.

(10) Patent No.: US 10,811,816 B2
(45) Date of Patent: Oct. 20, 2020

(54) CHIP ASSEMBLY FOR REUSABLE SURGICAL INSTRUMENTS

(71) Applicant: Covidien LP, Mansfield, MA (US)

(72) Inventors: Christopher Penna, Guilford, CT (US); Anthony Sgroi, Jr., Wallingford, CT (US); Charlie Kollar, West Hartford, CT (US); David Valentine, East Hampton, CT (US); Justin Williams, Southbury, CT (US); Patrick Mozdzierz, Glastonbury, CT (US); Stephen Paul, East Hartford, CT (US); Ramiro Cabrera, Cheshire, CT (US); Steven Joyce, Wallingford, CT (US); Joseph Guerrera, Watertown, CT (US)

(73) Assignee: Covidien LP, Mansfield, MA (US)

( * ) Notice: Subject to any disclaimer, the term of this patent is extended or adjusted under 35 U.S.C. 154(b) by 235 days.

(21) Appl. No.: 15/920,050

(22) Filed: Mar. 13, 2018

(65) Prior Publication Data

US 2018/0233850 A1 Aug. 16, 2018

Related U.S. Application Data

(63) Continuation-in-part of application No. 13/968,634, filed on Aug. 16, 2013, now Pat. No. 9,833,235.

(51) Int. Cl.
*A61B 17/115* (2006.01)
*H01R 13/52* (2006.01)
(Continued)

(52) U.S. Cl.
CPC ...... *H01R 13/5224* (2013.01); *A61B 17/1155* (2013.01); *A61B 90/90* (2016.02);
(Continued)

(58) Field of Classification Search
USPC ........................................... 227/176.1
See application file for complete search history.

(56) References Cited

U.S. PATENT DOCUMENTS

| 4,731,058 A | 3/1988 | Doan |
| 5,391,166 A | 2/1995 | Eggers |

(Continued)

FOREIGN PATENT DOCUMENTS

| EP | 2823774 A2 | 1/2015 |
| EP | 2875785 | 5/2015 |

(Continued)

OTHER PUBLICATIONS

European Search Report dated Dec. 4, 2019, issued in EP Appln. No. 19162099.

(Continued)

*Primary Examiner* — Michelle Lopez
*Assistant Examiner* — Chinyere J Rushing-Tucker
(74) *Attorney, Agent, or Firm* — Carter, DeLuca & Farrell LLP

(57) ABSTRACT

An improved chip assembly for use in a stapling device includes a housing assembly receivable within a reload assembly. The housing assembly includes a base member defining a cavity and an identification assembly received within the cavity. The chip assembly further includes a plug assembly configured to selectively engage the base member. The plug assembly includes a housing, a wire extending from the housing, a seal member disposed within and extending from a distal end of the housing, and first and second contact members extending through the seal member and from the housing. The seal member is configured to be frictionally received within the base member to secure the plug assembly to the housing assembly in a fluid tight manner.

13 Claims, 18 Drawing Sheets

(51) Int. Cl.
  *H01R 12/71* (2011.01)
  *H01L 23/00* (2006.01)
  *H01L 23/498* (2006.01)
  *A61B 90/90* (2016.01)
  *A61B 90/98* (2016.01)
  *A61B 17/00* (2006.01)
  *A61B 90/00* (2016.01)
  *H01R 13/627* (2006.01)
  *H01R 33/06* (2006.01)
  *H01R 13/66* (2006.01)

(52) U.S. Cl.
  CPC ........ *A61B 90/98* (2016.02); *H01L 23/49861* (2013.01); *H01L 24/08* (2013.01); *H01R 12/712* (2013.01); *H01R 13/5219* (2013.01); *A61B 2017/00017* (2013.01); *A61B 2017/0023* (2013.01); *A61B 2017/0046* (2013.01); *A61B 2017/00398* (2013.01); *A61B 2017/00473* (2013.01); *A61B 2017/00477* (2013.01); *A61B 2090/0803* (2016.02); *A61B 2090/0814* (2016.02); *H01L 24/13* (2013.01); *H01L 24/14* (2013.01); *H01L 24/16* (2013.01); *H01L 24/17* (2013.01); *H01L 24/81* (2013.01); *H01L 2224/08245* (2013.01); *H01L 2224/13101* (2013.01); *H01L 2224/14131* (2013.01); *H01L 2224/16245* (2013.01); *H01L 2224/17106* (2013.01); *H01L 2224/81815* (2013.01); *H01L 2924/14511* (2013.01); *H01R 13/6278* (2013.01); *H01R 13/6691* (2013.01); *H01R 33/06* (2013.01); *H01R 2201/12* (2013.01)

(56) References Cited

U.S. PATENT DOCUMENTS

| | | | | |
|---|---|---|---|---|
| 5,454,825 | A * | 10/1995 | Van Leeuwen | A61B 17/11 227/175.1 |
| 5,792,165 | A * | 8/1998 | Klieman | A61B 17/29 606/170 |
| 7,721,931 | B2 | 5/2010 | Shelton, IV et al. | |
| 7,887,530 | B2 | 2/2011 | Zemlok et al. | |
| 8,397,971 | B2 | 3/2013 | Yates et al. | |
| 9,833,235 | B2 | 12/2017 | Penna et al. | |
| 2001/0031975 | A1 * | 10/2001 | Whitman | A61B 10/0233 606/167 |
| 2007/0023477 | A1 | 2/2007 | Whitman et al. | |
| 2007/0175964 | A1 * | 8/2007 | Shelton, IV | A61B 17/00 227/180.1 |
| 2009/0057369 | A1 | 3/2009 | Smith et al. | |
| 2009/0090763 | A1 * | 4/2009 | Zemlok | A61B 17/07207 227/175.2 |
| 2011/0125138 | A1 | 5/2011 | Malinouskas et al. | |
| 2011/0155784 | A1 | 6/2011 | Shelton, IV et al. | |
| 2011/0174862 | A1 * | 7/2011 | Shelton, IV | A61B 17/07207 227/176.1 |
| 2011/0192884 | A1 | 8/2011 | Whitman et al. | |
| 2011/0290854 | A1 * | 12/2011 | Timm | A61B 17/32 227/178.1 |
| 2012/0071866 | A1 | 3/2012 | Kerr et al. | |
| 2012/0209288 | A1 | 8/2012 | Robinson | |
| 2012/0323226 | A1 * | 12/2012 | Chowaniec | A61B 17/072 606/1 |
| 2013/0123822 | A1 | 5/2013 | Wellman et al. | |
| 2013/0131650 | A1 | 5/2013 | Whitman et al. | |
| 2013/0319706 | A1 * | 12/2013 | Nicholas | A61B 90/98 173/29 |
| 2014/0226295 | A1 | 8/2014 | Nishio et al. | |
| 2015/0216525 | A1 * | 8/2015 | Collins | H05K 7/06 227/176.1 |
| 2015/0351765 | A1 * | 12/2015 | Valentine | A61B 90/90 227/176.1 |
| 2017/0181745 | A1 | 6/2017 | Penna et al. | |

FOREIGN PATENT DOCUMENTS

| | | |
|---|---|---|
| JP | H06304176 A | 11/1994 |
| JP | 2005520593 A | 7/2005 |
| JP | 2010540192 A | 12/2010 |
| JP | 20105400041 | 12/2010 |
| WO | 2013051076 A1 | 4/2013 |

OTHER PUBLICATIONS

European Search Report EP14181110 dated Feb. 26, 2015.
European Office Action issued in corresponding European Application No. EP14181110.9 dated Mar. 1, 2016.
Maxim Integrated Brochure (Abridged Data Sheet)—DeepCover Secure Authenticator with 1-Wire SHA-256 and 512-Bit User EEPROM, pp. 1-4 and p. 42, 2012.
"IC-On-Line" DS28E15-1-Wire SHA-256 Secure Authenticator with 512-Bit User EEPROM, located at: <http://www.ic-on-line.cn/view.sub.--download>.
Chinese Office Action dated May 3, 2018 in Chinese Appln. No. 2014104044066.
Japanese Office Action dated May 14, 2018 in JP Appln. No. 2014164761.

* cited by examiner

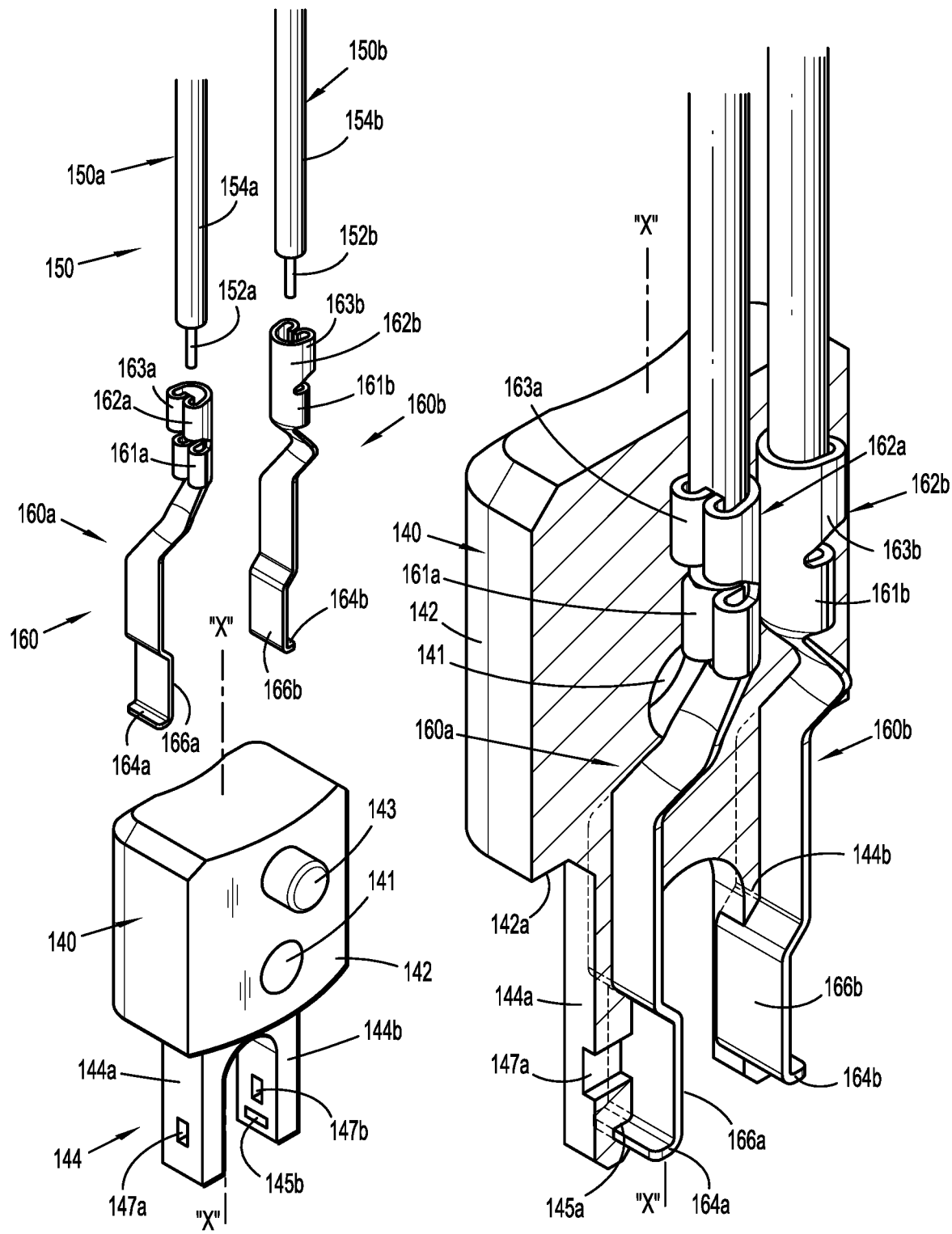

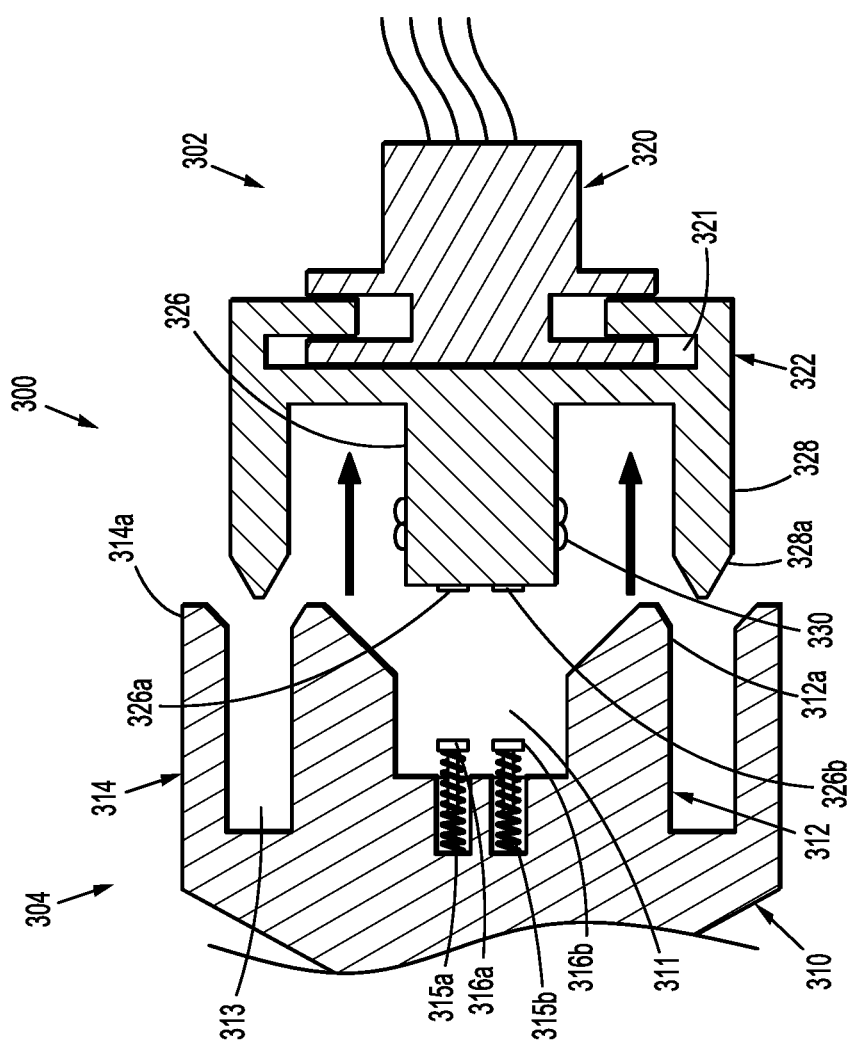

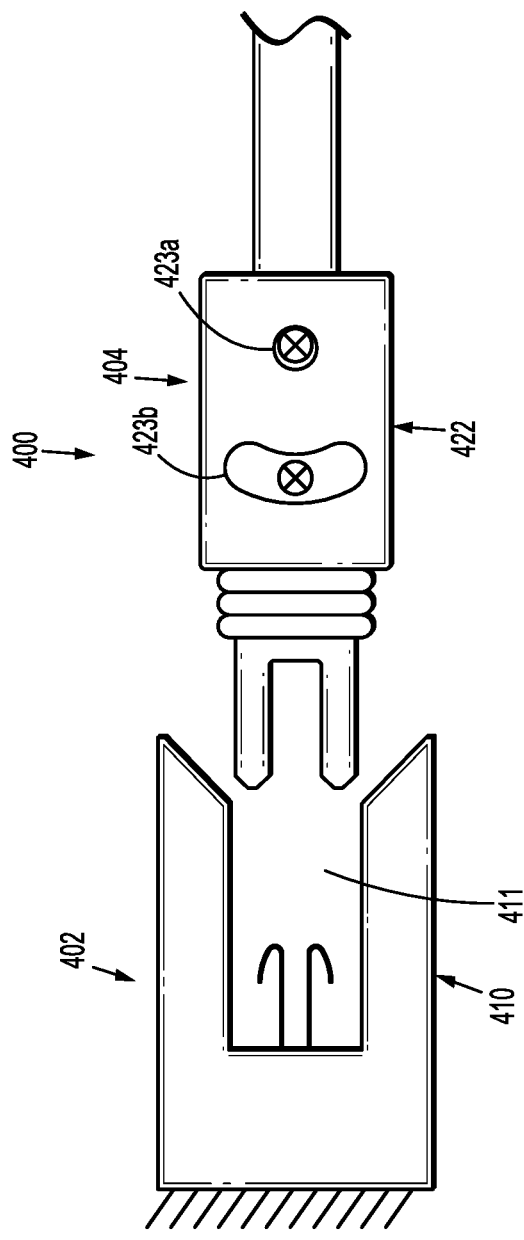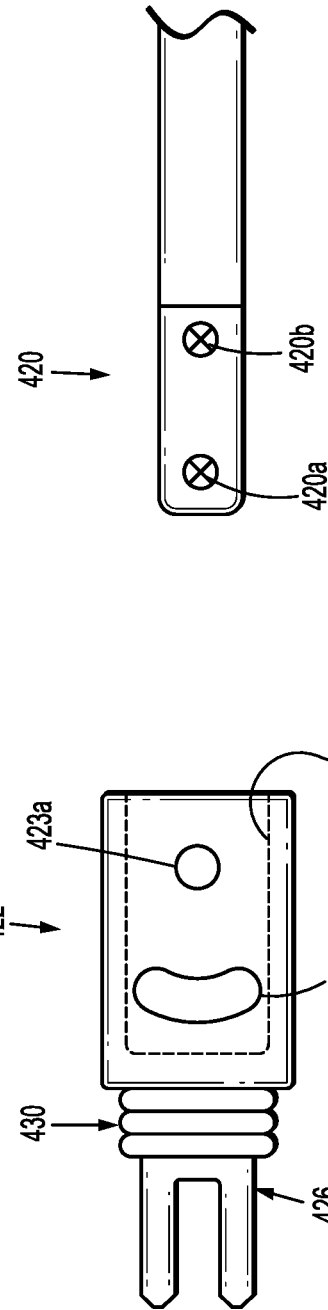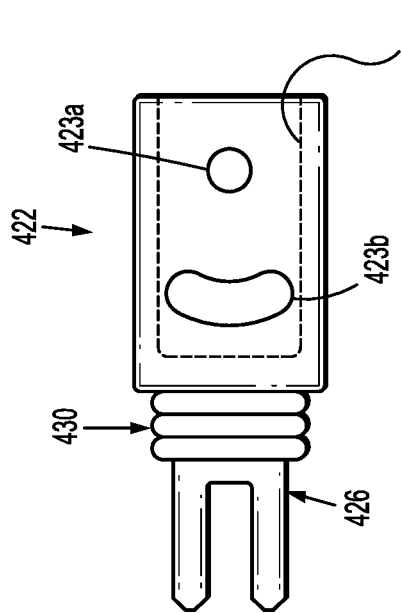

CHIP ASSEMBLY FOR REUSABLE SURGICAL INSTRUMENTS

CROSS-REFERENCE TO RELATED APPLICATIONS

The present application is a continuation in part of U.S. patent application Ser. No. 13/968,634, filed Aug. 16, 2013, (now U.S. Pat. No. 9,833,235) the content of which is incorporated herein by reference in its entirety.

BACKGROUND

Technical Field

The present disclosure relates to surgical instruments having a reusable handle and a disposable end effector. More particularly, the present disclosure relates to a chip assembly for use in a stapling instrument having a disposable loading unit.

Background of Related Art

Powered surgical instruments for use in endoscopic procedures are known. Typically, such instruments include a reusable handle assembly and a disposable end effector. An adapter assembly connects the end effector to the handle assembly. In the case of a surgical stapler, the end effector includes a disposable cartridge or reload assembly that is changed after each firing of the surgical stapler. To reduce costs and shorten procedure times, the handle assemblies are generally configured for use with a variety of reload assemblies of various configurations for use on tissue having different properties, i.e., thickness, density. For example, the different reload assemblies may have staples of different sizes and/or the staples may be arranged in different configurations. To ensure the handle assembly is programmed to operate with the attached reload assembly, some reload assemblies are provided with a chip that communicates to the handle assembly the configuration of the reload assembly. As such, the configuration of the reload assembly is automatically relayed to the handle assembly upon attachment of the reload assembly to the adapter assembly, thereby eliminating any user error that may be experienced during manual programming of the handle assembly when switching between reload assemblies with different configurations.

Surgical staplers are generally used for stapling tissue within a body cavity where the end effector is likely to come in contact with fluids, i.e., blood, bile, irrigation solutions. If any fluids were to contact the chip or the connections between the chip and the handle assembly, the chip would short-circuit, rendering the surgical stapler inoperable.

Therefore, it would be beneficial to have a chip assembly configured to limit exposure of the chip and the connections between the chip and the handle assembly to fluids during a stapling procedure.

SUMMARY

Accordingly, an improved chip assembly for use in a stapling device is provided. The chip assembly includes a housing assembly receivable within a reload assembly. The housing assembly including a base member defining a cavity and an identification assembly received within the cavity. The chip assembly further includes a plug assembly configured to selectively engage the base member. The plug assembly includes a housing, a wire extending from the housing, a seal member disposed within and extending from a distal end of the housing, and first and second contact members extending through the seal member and from the housing. The seal member is configured to be frictionally received within the base member to secure the plug assembly to the housing assembly in a fluid tight manner.

In embodiments, the identification assembly includes first and second contact members and a chip. The chip may be a 1-Wire Chip. The chip may be secured directly to the first and second contact members. The chip may be soldered directly to the first and second contact members. The chip may be an EPROM chip.

In embodiments, the plug assembly further includes first and second contact members configured to selectively engage the respective first and second contact members of the housing assembly when the plug assembly is engaged with the base member of the housing assembly. The first and second contact members of the plug assembly may be configured to engage the chip member contact when the plug assembly engages the housing assembly. The housing may include first and second half sections. The base member may include an open end having a tapered surface configured to facilitate receipt of the seal member within the base member. The seal member may include ridges configured to facilitate a friction fit between the housing assembly and the plug assembly.

Also provided is surgical stapling device including a handle assembly, an adapter assembly extending from the handle assembly, a reload assembly operably connected to a distal end of the adapter assembly, and a chip assembly including a housing assembly and a plug assembly. The housing assembly is receivable within a reload assembly and is configured for connection to a surgical stapler. The housing assembly includes a base member and an identification assembly. The identification assembly includes first and second contact members and a 1-Wire Chip secured directly to the first and second contact members. The plug assembly includes a seal member configured to selectively engage the base member in a fluid tight manner when the plug assembly is in engagement with the housing assembly.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 10 is an exploded view of the plug assembly shown in FIG. 6;

FIG. 11 is a cross-sectional perspective view of the plug assembly shown in FIG. 6;

FIG. 25 is a cross-sectional side view of a chip assembly according to yet another embodiment of the present disclosure, including a housing assembly and a plug assembly;

FIG. 28 is a side view of still yet another embodiment of the present disclosure, including a housing assembly and a plug assembly;

FIG. 29 is a side view of a fixed base of the plug assembly shown in FIG. 28;

FIG. 30 is a side view of a floating housing of the plug assembly shown in FIG. 28;

DETAILED DESCRIPTION

Figure 1:
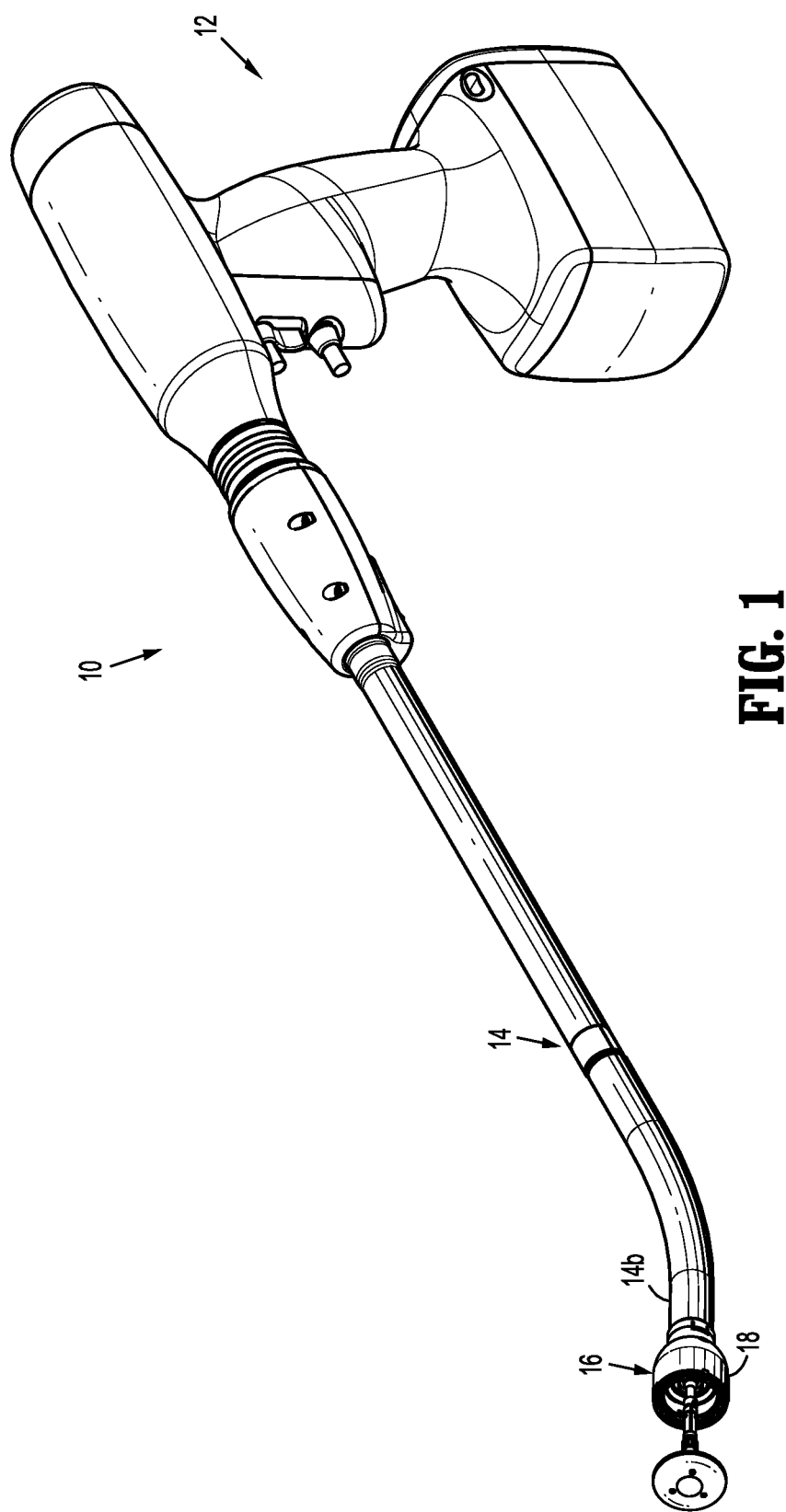
FIG. 1 is a perspective view of a surgical stapling device for use with a chip assembly according to embodiments of the present disclosure.

Embodiments of the presently disclosed chip assembly will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

With reference initially to FIG. 1, a surgical stapling instrument including a chip assembly according to the present disclosure is shown generally as circular stapler 10. The circular stapler 10 includes a handle assembly 12, an adapter assembly 14 extending distally from the handle assembly 12, and a reload assembly 16 selectively secured to a distal end 14b of the adapter assembly 14. A detailed description of exemplary handle assemblies and adapter assemblies is provided in commonly owned U.S. Pat. App. Pub. No. 2012/0089131, the content of which is incorporated herein by reference in its entirety.

Figure 2:
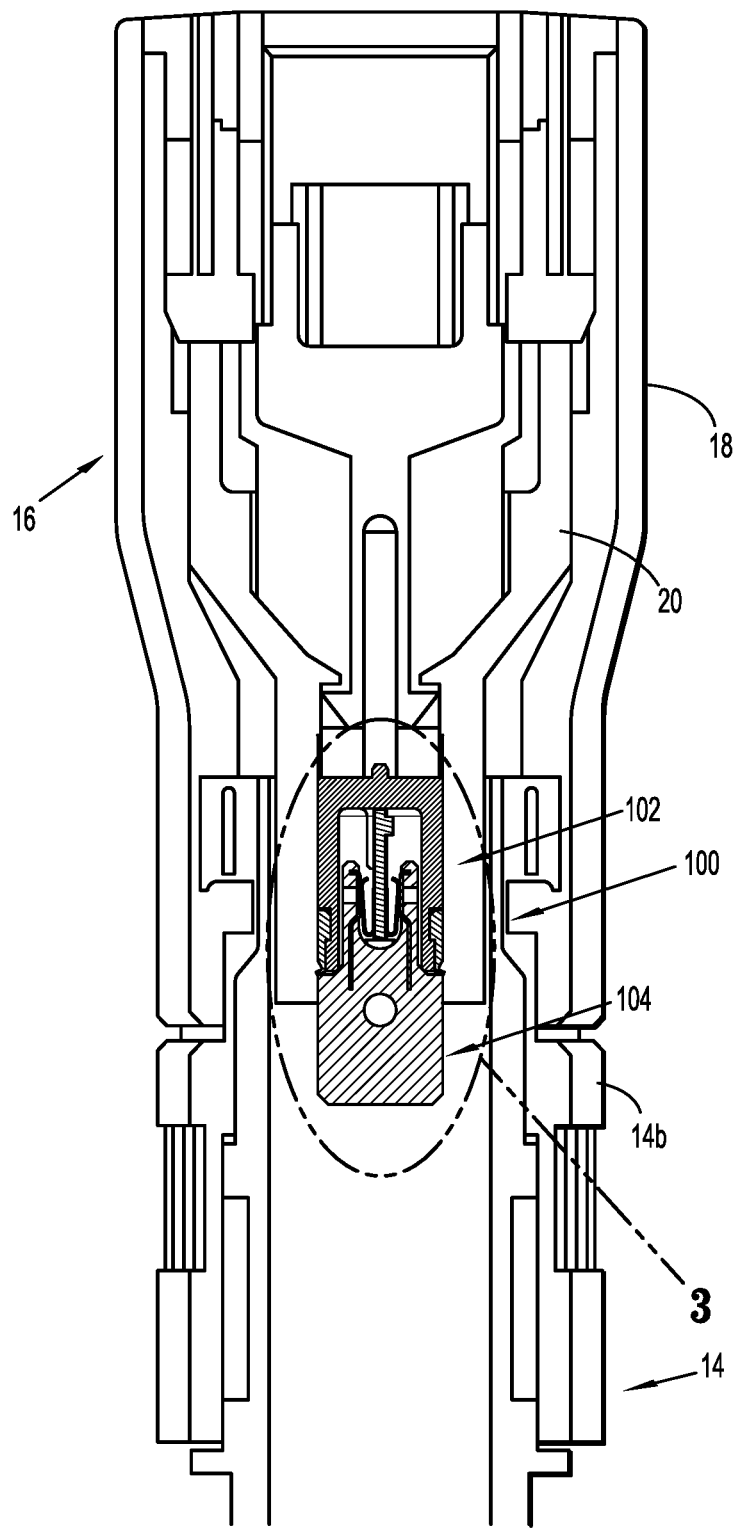
FIG. 2 is a cross-sectional view of the distal end of an adapter assembly and a reload assembly of the surgical stapling device shown in FIG. 1.

Turning briefly to FIG. 2, the reload assembly 16 of the circular stapler 10 (FIG. 1) includes a shell member 18 and a pusher member 20 slidably disposed within the shell member 18. A proximal end of the shell member 18 is selectively secured to the distal end 14b of the adapter assembly 14 by a slot and tab configuration. A proximal end of the pusher member 20 is selectively secured to a distal end of a driver member (not shown) in a similar fashion.

With reference now to FIGS. 2-11, the chip assembly 100 includes a housing assembly 102 and a plug assembly 104. As seen in FIG. 2, the housing assembly 102 is configured to be securely mounted within the reload assembly 16, and the plug assembly 104 is configured to be securely mounted within the distal end 14b of the adapter assembly 14. The housing assembly 102 and the plug assembly 104 are positioned within the respective reload assembly 16 and adapter assembly 14 such that when the reload assembly 16 is secured to the adapter assembly 14, the housing assembly 102 engages the plug assembly 104. It is envisioned that one or both of the housing assembly 102 and the plug assembly 104 may be spring biased towards the other to overcome any manufacturing tolerances between the reload assembly 16 and the adapter assembly 14. Alternatively, and as will be described in further detail below, one of the housing assembly or the plug assembly may include a floating connection wherein one of the housing assembly and the plug assembly is fixed, and the other of the housing assembly and the plug assembly includes a floating connector configured to self-align the housing assembly or the plug assembly. (See for example FIGS. 25-28).

With particular reference to FIGS. 5-8, the housing assembly 102 includes a base member 110, a seal member 120, and a circuit board assembly 130. The base member 110 defines a cavity 111 and includes an open first end 110a and a closed second end 110b. In one embodiment, the base member 110 is monolithically formed to ensure the cavity 111 is fluid tight. Alternatively, the base member 110 may be formed as two components that are joined together in a fluid tight manner, e.g., by welding or adhesive.

Still referring to FIGS. 5-8, the first end 110a of base member 110 of the housing assembly 102 forms an extension 112 configured to engage the seal member 120. Specifically, the extension 112 is formed by a laterally recessed portion of the base member 110. A flange 114 extends about an end of the extension 112 and is configured to engage a lip 122 on the seal member 120. The reduced outer dimension of the extension 112 allows the seal member 120 to lay flush with the base member 110. As can be appreciated with reference to FIG. 5, the flush configuration of the seal member 120 relative to the base member 110 reduces the likelihood of the seal member 120 from being separated from the base member 110 during use. The base member 110 further defines a slot 111a (see FIG. 7) in communication with the cavity 111. The slot 111a is configured to selectively receive the circuit board assembly 130. The extension 112 defines first and second notches 113a, 113b in alignment with the slot 111a. The first notch 113a is configured to receive a first inwardly extending tab 124a formed on the seal member 120. The second notch 113b is configured to receive a second inwardly extending tab 124b formed on the seal member 120. As will be discussed in further detail below, either or both of the tabs 124a, 124b may be configured to retain the circuit board assembly 130 within the slot 111a of base member 110.

With reference still to FIGS. 5-8, the base member 110 of the housing assembly 102 includes a support member 116 (see FIG. 3) extending from the closed second end 110b into the cavity 111. The support member 116 is configured to the support circuit board assembly 130 when the circuit board assembly 130 is received within the slot 111a of the base member 110. The base member 110 further includes a connection member 118 for securing the housing assembly 102 within the reload assembly 16 (FIG. 2). As shown, the connection member 118 includes an annular flange 118a extending perpendicular to a longitudinal axis "x" of the base member 110. The annular flange 118a is configured to be received about a tubular sleeve 22 (FIG. 4) of the reload assembly 16. Although shown as the annular flange 118a, it is envisioned that the connection member 118 may include a C-shaped flange (not shown) for selective attachment to the reload assembly 16. In embodiments, the connection member 118 may include one or more tabs and/or one or more slots for connection of the reload assembly 116 to the base member 110 through a tab and slot configuration.

The base member 110 of the housing assembly 102 further includes one or more alignment features 119. As shown, the alignment feature 119 forms a protrusion extending outwardly from the closed second end 110b of the base member 110. The alignment feature 119 facilitates alignment of the base member 110 within the reload assembly 16 and/or prevents rotational movement of the housing assembly 102 during transport, loading, and use of the reload assembly 16.

With continued reference to FIGS. 5-8, the seal member 120 of the housing assembly 102 includes a substantially annular body having open first and second ends 120a, 120b. The first end 120a includes the lip 122 extending about an inner surface of the seal member 120. As discussed above, the lip 122 is configured to engage the flange 114 formed on the extension 112 of the base member 110. In this manner, the seal member 120 forms a fluid tight seal about the extension 112 of the base member 110. Optionally, the seal member 120 is adhered or otherwise bonded to the extension 112 to increase the integrity of the seal between the seal member 120 and the base member 110.

The second end 120b of the seal member 120 includes the first and second inwardly extending tabs 124a, 124b. As discussed above, the first tab 124a is configured to be received within the first notch 113a defined by the extension 112 of the base member 110 and the second tab 124b (FIGS. 6 and 9) is configured to be received within the second notch 113b defined by the extension 112 of the base member 110 when the seal member 120 is secured to the base member 110. At least the first tab 124a is configured to ensure the circuit board assembly 130 is maintained within the slot 111a formed in the base member 110. A flap 126 extends from the second end 120b of the seal member 120 and is configured to form a seal between the housing assembly 102 and the plug assembly 104 when the plug assembly 104 engages the housing assembly 102.

Figure 8:
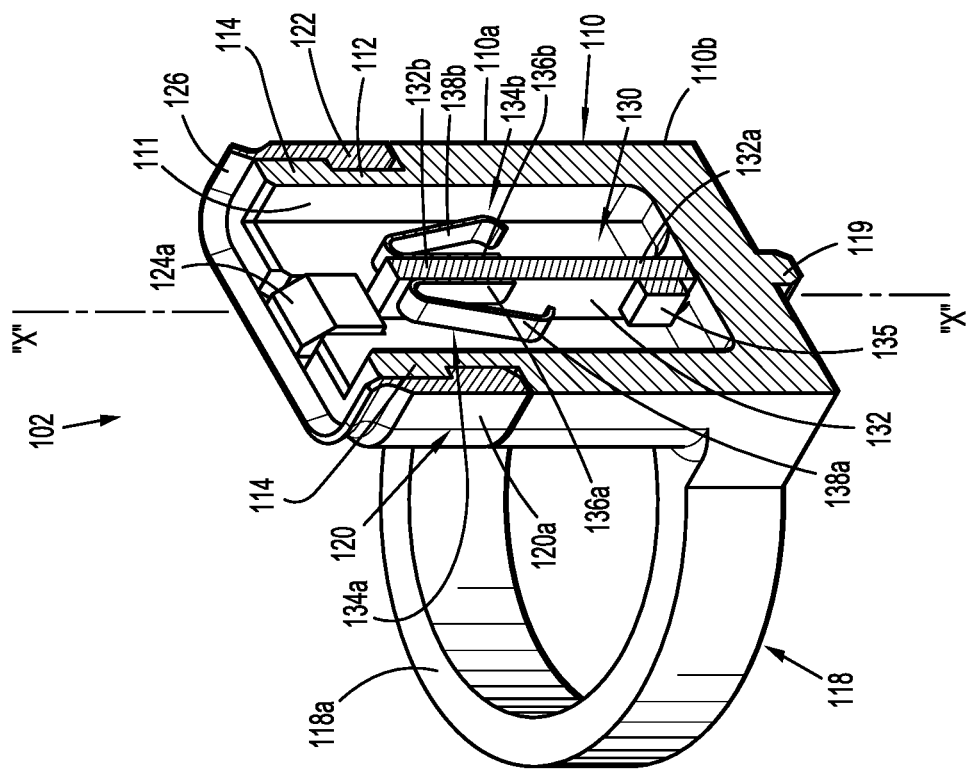
FIG. 8 is a cross-sectional perspective view of the housing assembly shown in FIG. 6.
Figure 7:
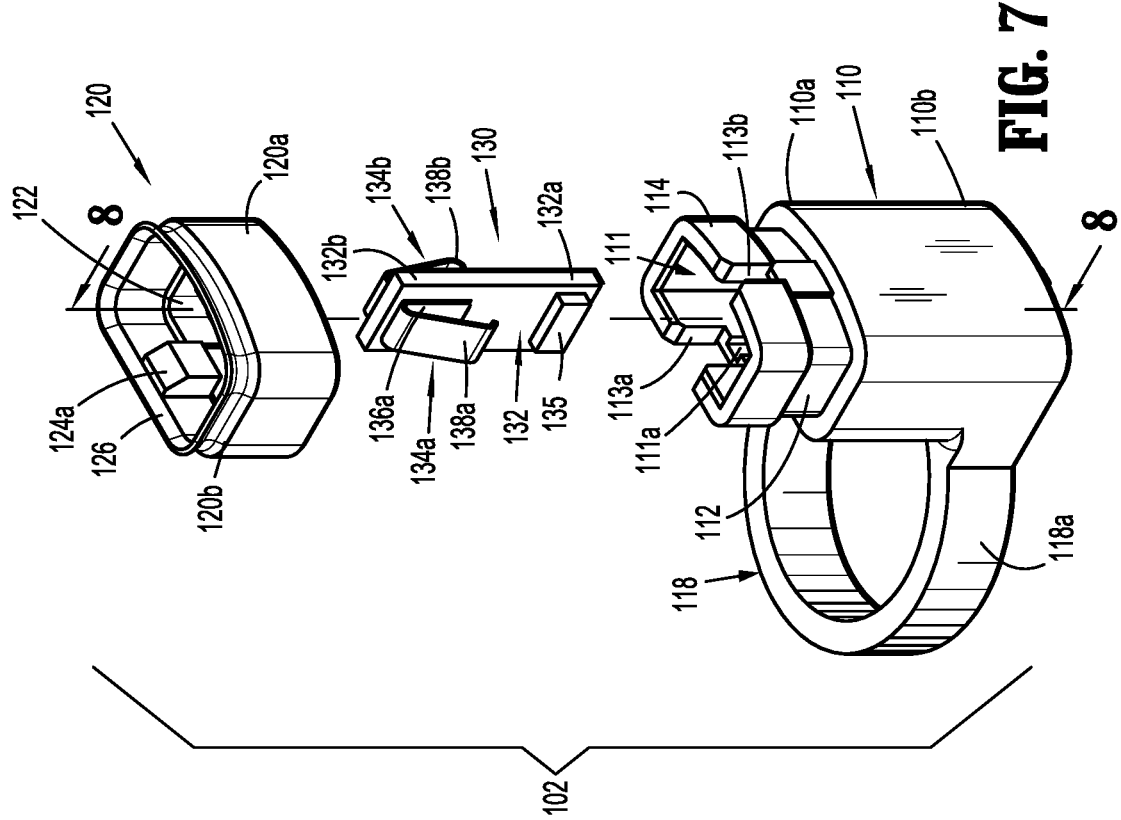
FIG. 7 is an exploded perspective view of the housing assembly shown in FIG. 6.
Figure 9:
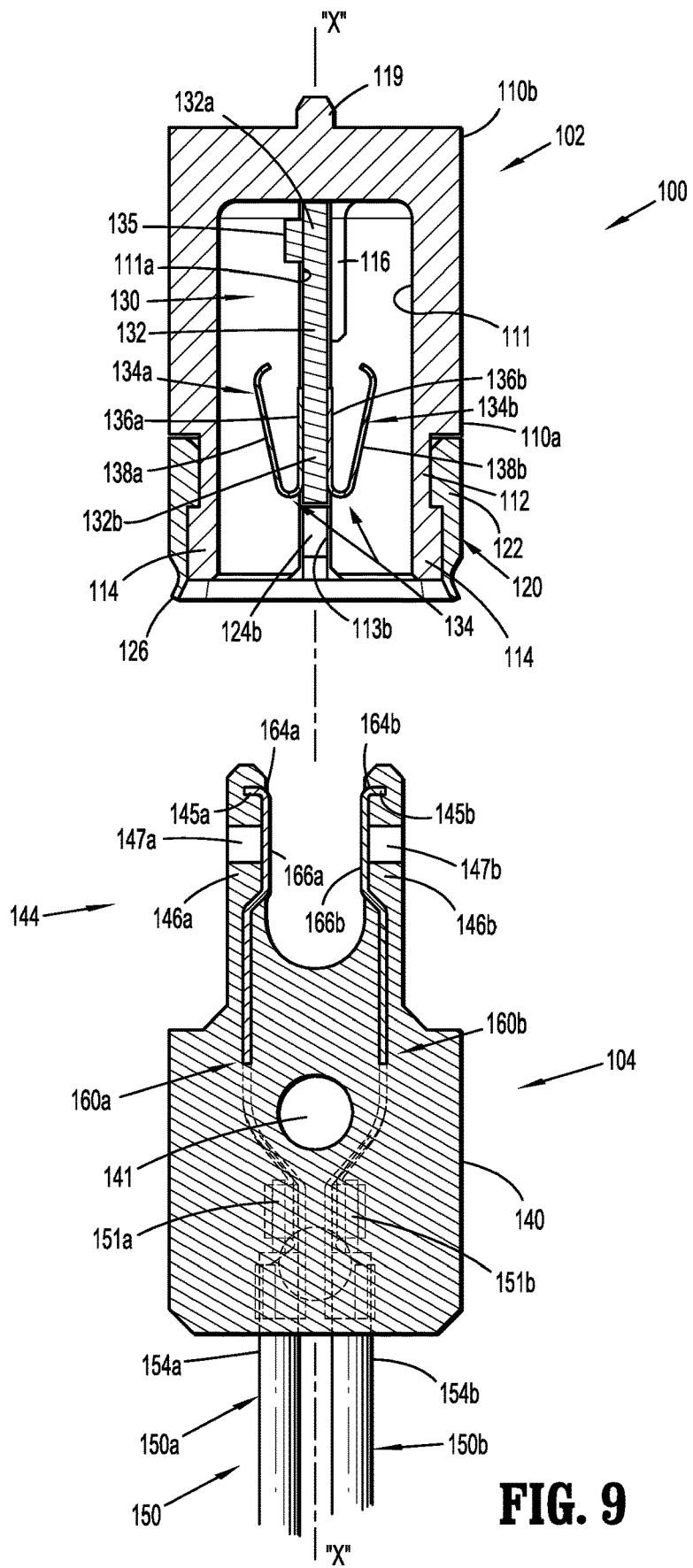
FIG. 9 is a cross-sectional side view of the housing assembly and plug assembly shown in FIG. 6.

With particular reference now to FIGS. 7-9, the circuit board assembly 130 of the housing assembly 102 includes a circuit board 132, a pair of contact members 134a, 134b (collectively, contact members 134), and a chip 135. The circuit board 132 defines a substantially planar elongate member configured to be securely received within the slot 111a defined by the base member 110. The chip 135 is in electrical communication with the contact member 134. A first end 132a of the circuit board 132 supports the chip 135, and a second end 132b of the circuit board 132 supports the first and second contact members 134a, 134b.

The chip 135 of the circuit board assembly 130 includes any commercially available chip capable of storing the specifications of the reload assembly 16, e.g., cartridge size, staple arrangement, staple length, clamp-up distance, and transmitting the specifications to the handle assembly 12. In one embodiment, the chip 135 includes an erasable or electrically erasable programmable read only memory ("EPROM" or "EEPROM") chip. In this manner, the firing forces and/or firing stroke of the handle assembly 12 may be adjusted to accommodate the attached the reload assembly 16. It is further envisioned that the chip 135 may include write capabilities which allow the handle assembly 12 to encode that a reload assembly has been used to the chip 135 to prevent reuse of an empty reload assembly, or for any other purpose.

Figure 3:
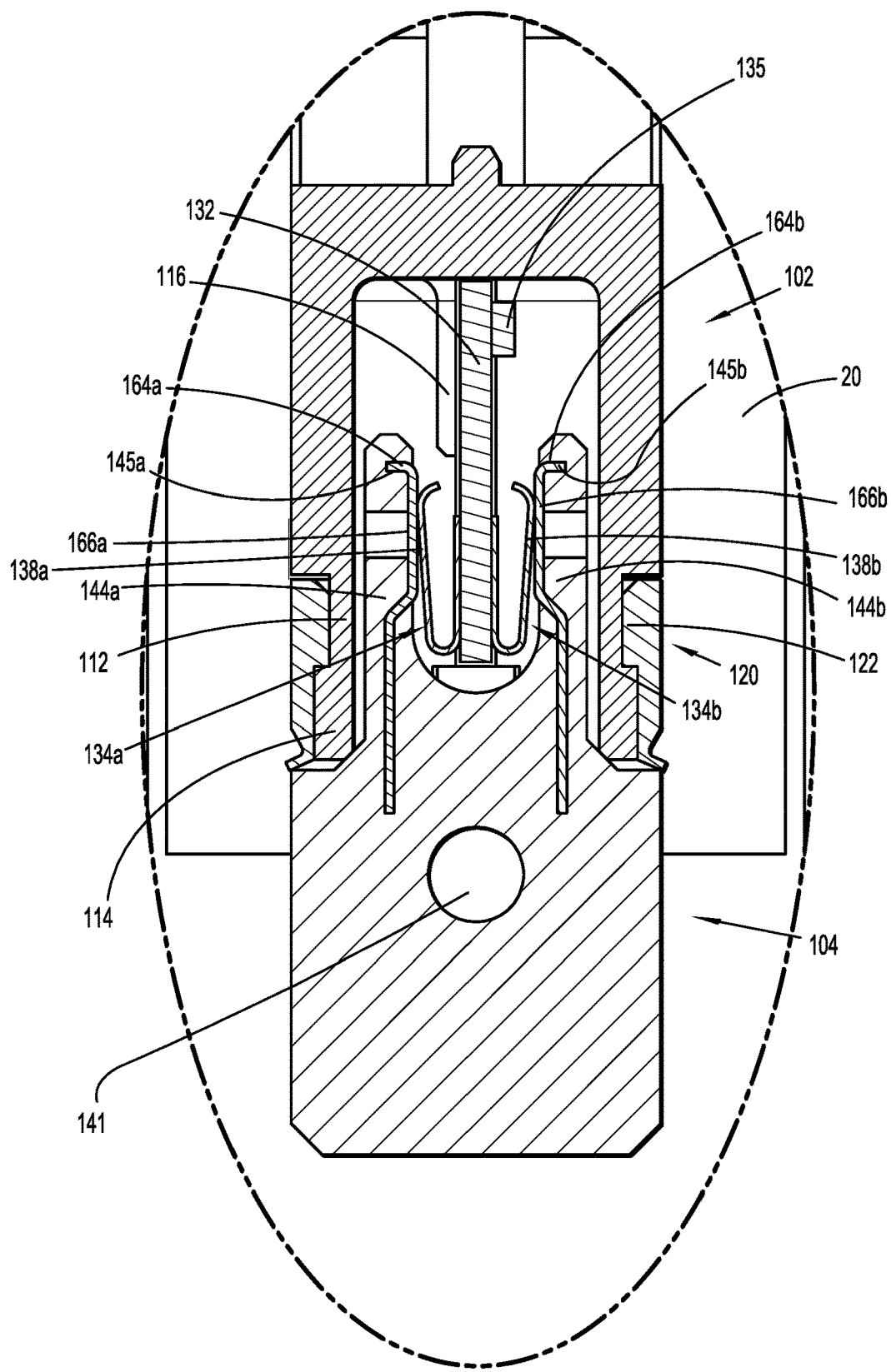
FIG. 3 is an enlarged view of the indicated area shown in FIG. 2.
Figure 4:
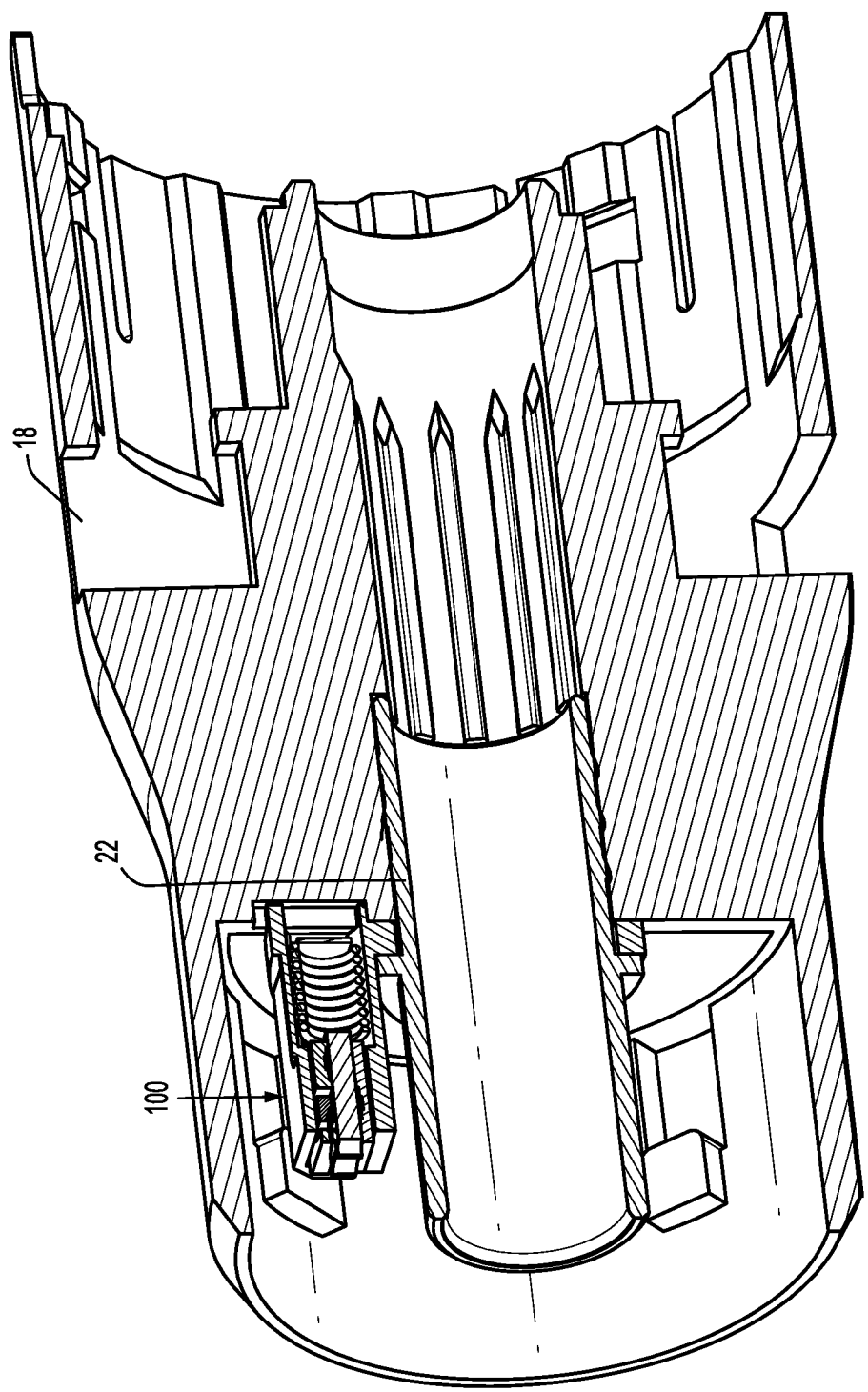
FIG. 4 is another cross-sectional view of the reload assembly shown in FIG. 1.
Figures 5, 6:
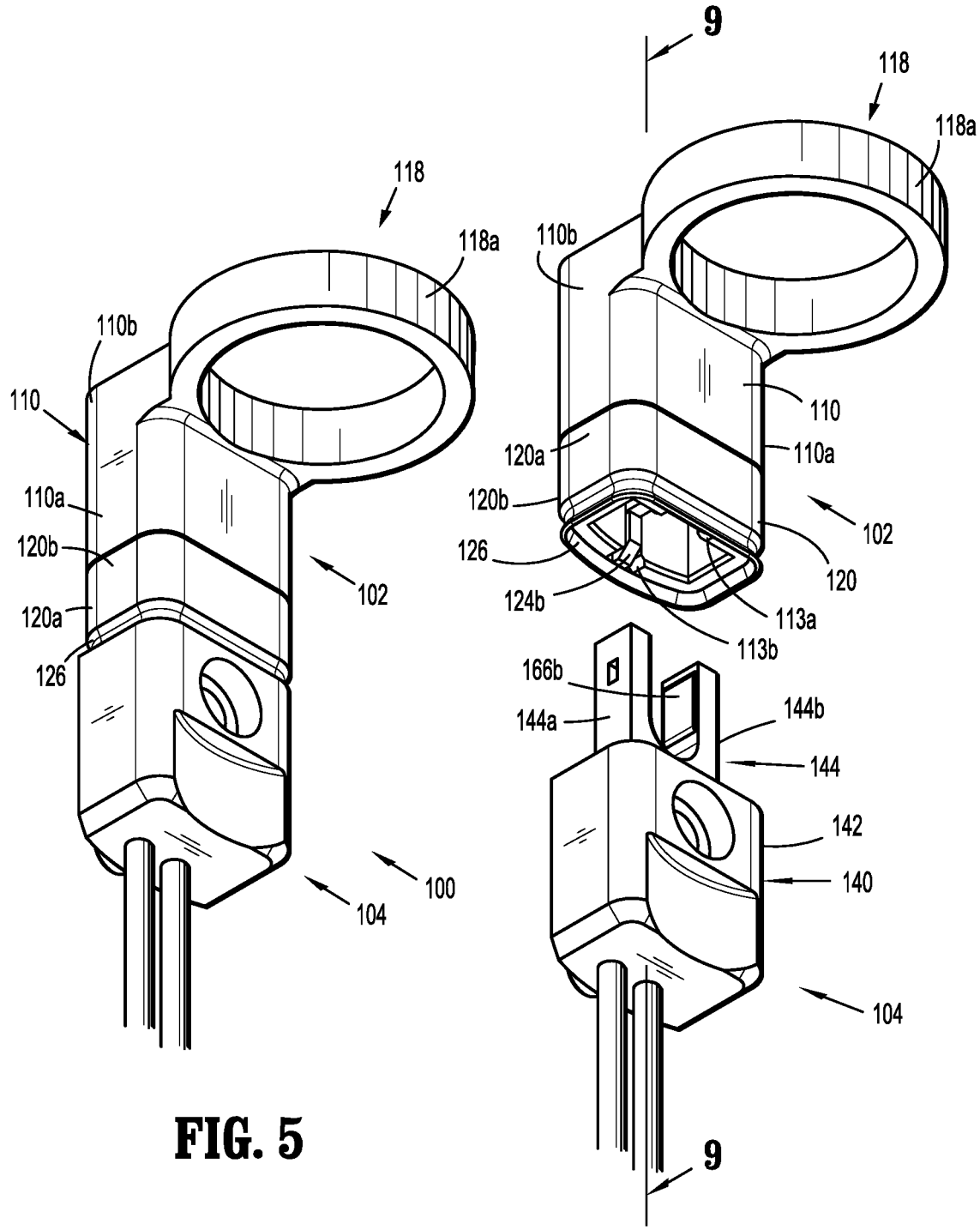
FIG. 5 is a perspective view of a chip assembly according to an embodiment of the present disclosure.
FIG. 6 is a perspective view of the chip assembly shown in FIG. 5 with a housing assembly and a plug assembly separated.

With reference still to FIGS. 7-9, the contact members 134a, 134b each include leaf contacts having a substantially flattened C-shape. A flange portion 136a, 136b of first and second contact members 134a, 134b is secured to second end 132b of circuit board 132 using adhesive, welding, soldering or other method. A contact portion 138a, 138b of each of contact members 134a, 134b extends outwardly from the flange portion 136a, 136b, respectively, and includes respective contact surface 135a, 135b. As seen in FIG. 3, the contact portions 138a, 138b of the contact members 134a, 134b extend outward an amount sufficient to ensure contact between the contact portions 138a, 138b of the contact members 134a, 134b, respectively, and the plug assembly 104.

Turning now to FIGS. 9-11, the plug assembly 104 includes a plug member 140, first and second wires 150a, 150b (collectively, wires 150), and a first and second contact members 160a, 160b (collectively, contact members 160). The plug member 140 includes a substantially rectangular base 142 defining a longitudinal axis "x" and a pair of arms 144a, 144b (collectively, arms 144) extending from the base 142 parallel to and spaced from longitudinal axis "x". A shelf 142a extends around the arms 144 and is configured to be engaged by the flap 126 (FIG. 9) of the seal member 120 when the arms 144 of the plug assembly 104 are operatively received within the cavity 111 of the housing assembly 102.

As shown, the base 142 defines an opening 141 extending perpendicularly through the plug member 140 and includes an annular protrusion 143 extending perpendicularly outward from the plug member 140. As shown, the protrusion 143 is adjacent the opening 141. Either or both of the opening 141 and the protrusion 143 may be used to secure the plug assembly 104 to the adapter assembly 14 of the circular stapler 10 (FIG. 1). The first and second arms 144a, 144b are sized and dimensioned to be received within the cavity 111 of the base member 110 and about the circuit board assembly 130 when the circuit board assembly 130 is received within the slots 111a defined by the base member 110.

In embodiments, the plug member 140 is composed of plastic or other moldable material that is formed over the contact members 160 after the wires 150 are secured to the respective first and second contact members 160a, 160b. In this manner, the connection between the contact members 160 and the wires 150 is sealed from any possible contact with fluids, bodily or otherwise, during a stapling procedure. Alternatively, the plug member 140 may include two components that are joined in a fluid tight manner, i.e., welding, adhesive.

With reference still to FIGS. 9-11, a first end of each of the first and second contact members 160a, 160b includes a wire connection portion 162a, 162b, respectively, for securing first and second wires 150a, 150b to the first and second contact members 160a, 160b, respectively. As shown, the wire connection portion 162a, 162b each include a first crimp member 161a, 161b (FIG. 10) configured to be crimped about an exposed portion 152a, 152b of the respective, first and second wires 150a, 150b, and a second crimp member 163a, 163b (FIG. 10) configured to be crimped about the respective coated portions 154a, 154b of the first and second wires 150a, 150b, respectively. Alternatively, the wires 150a, 150b may be welded or soldered directly to respective first and second contact members 160a, 160b.

Still referring to FIGS. 9-11, a second end of each of the first and second contact members 160a, 160b includes a flange 164a, 164b, respectively and a contact portion 166a, 166b, respectively. The contact portions 166a, 166b of the respective first and second contact members 160a, 160b are configured to engage the respective contact portions 138a, 138b of the contact members 134a, 134b extending outwardly from the circuit board 132 of the circuit board assembly 130.

As noted above, in embodiments, the plug member 140 is formed by molding the base 142 and the arms 144 about the wires 150 and the contact members 160. Specifically, after the first and second wires 150a, 150b have been secured to the connection portion 162a, 162b of the respect first and second contact members 160a, 160b, the base 142 of the plug member 140 is formed over the first ends of the first and second contact members 160a, 160b and the first and second arms 144a, 144b are formed about the second ends of first and second contact members the 160a, 160b, respectively. The first and second arms 144a, 144b are formed about the respective first and second contact members 160a, 160b such that the respective contact portions 166a, 166b remain exposed. The forming of the first and second arms 144a, 144b about the flanges 164a, 164b of the first and second contact members 160a, 160b creates slots 145a, 145b in the respective first and second arms 144a, 144b. Alternatively, the first and second arms 144a, 144b are formed with the slots 145a, 145b, respectively, to receive the flanges 164a, 164b, respectively. The first and second arms 144a, 144b each define a throughbore 147a, 147b, respectively, extending perpendicular to the longitudinal axis "x".

The operation of the chip assembly 100 will now be described with reference to FIGS. 2-11. Although the adapter assembly 14 and the reload assembly 16 are typically provided to a clinician with the plug assembly 104 mounted within the adapter assembly 14 and the housing assembly 102 mounted within the adapter assembly 14, it is envisioned, that either or both of the housing assembly 102 and the plug assembly 104 may be secured within the respective adapter assembly 14 and reload assembly 16 by a clinician prior to use. Although not shown, it is envisioned that either or both of the housing assembly 102 and the plug assembly 104 may be spring loaded within the respective reload assembly 16 and adapter assembly 14 to allow for positional length tolerances between the reload assembly 16 and the adapter assembly 14.

As noted above, the housing assembly 102 is disposed within the reload assembly 16 such that when the reload assembly 16 is secured to the adapter assembly 14, the housing assembly 102 engages the plug assembly 104. Specifically, when the reload assembly 16 is secured to the adapter assembly 14, the first and second arms 144a, 144b of the plug assembly 104 are received within the cavity 111 of the housing assembly 102 such that the contact portions 166a, 166b of the respective first and second contact members 160a, 160b engage the respective contact portions 138a, 138b of the respective first and second contact members 134a, 134b of the circuit board assembly 130.

The outward extension of the contact portions 138a, 138b of the first and second contact members 134a, 134b ensures contact between the contact portions 166a, 166b of the respective first and second contact members 160a, 160b and the contact portions 138a, 138b of the respective first and second contact members 134a, 134b. The sweeping motion provided by the spring-like action of the contact portions 138a, 138b of the respective first and second contact members 134a, 134b further ensures positive contact between the first and second contact members 134a, 134b, respectively, of the housing assembly 102 and the first and second contact members 160a, 160b, respectively. Once the housing assembly 102 is connected to the plug assembly 104, within the adapter assembly 114, it is envisioned that the chip 135 will automatically transmit the specifications of the reload assembly 16 to the handle assembly 12 to ensure the handle assembly 12 is configured for use with the reload assembly 16.

As discussed above, the seal member 120 of the housing assembly 102 includes the flap 126 which engages the shelf 142a formed on the base 142 of the plug assembly 104 to create a seal between the housing assembly 102 and the plug assembly 104. Since the contact portions 138a, 138b of the respective first and second contact members 134a, 134b and the contact portions 166a, 166b of the respective first and second contact members 160a, 160b are maintained completely within the cavity 111 formed in the base member 110 of the housing assembly 102, the flap 126 of the seal member 120 prevents exposure of the contact members 134a, 134b, 160a, 160b to any fluids encountered by the circular stapler 10 during a stapling procedure. Once the circular stapler 10 has been used, the reload assembly 16 may be separated from the adapter assembly 14 in a traditional manner. A replacement reload assembly 16 may then be secured to the adapter assembly 14 for further use of the circular stapler 10.

With reference now to FIGS. 12-24, a chip assembly according to another embodiment of the present disclosure is shown generally as chip assembly 200. The chip assembly 200 is substantially similar to the chip assembly 100 described hereinabove, and will only be described in detail as relates to the differences therebetween.

Figure 13:
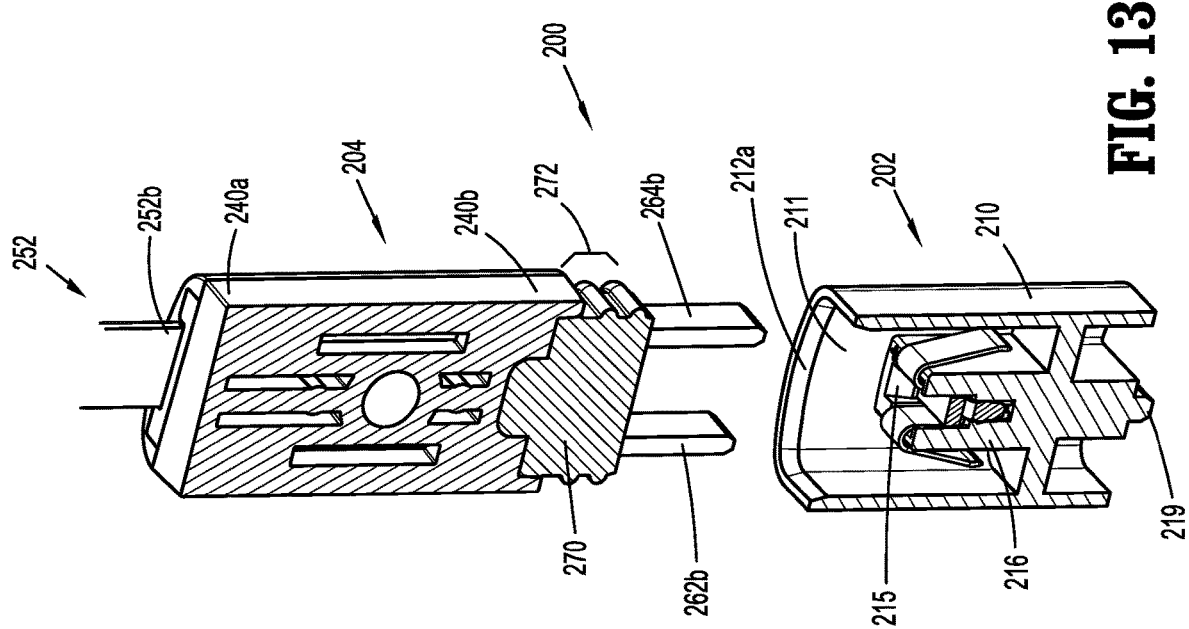
FIG. 13 is cross-sectional side view taken along line 13-13 shown in FIG. 12.
Figure 12:
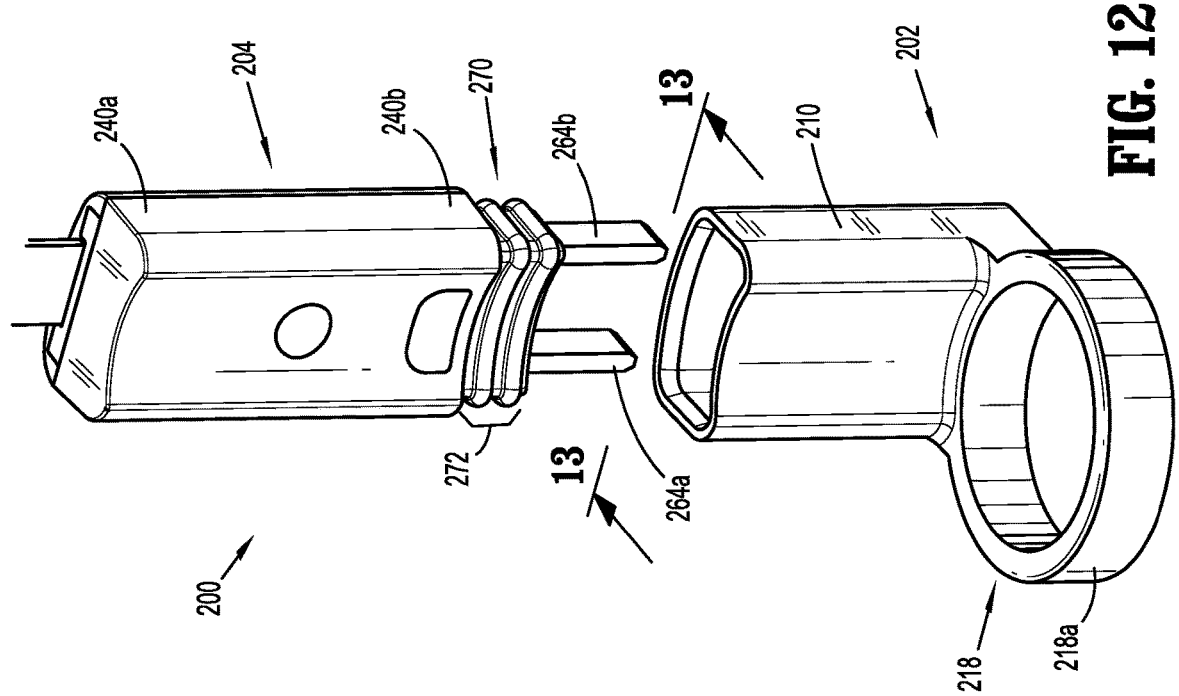
FIG. 12 is a perspective view of a chip assembly according to another embodiment of the present disclosure, illustrating a housing assembly and a plug assembly thereof separated.

With initial reference to FIGS. 12 and 13, the chip assembly 200 includes a housing assembly 202, and a plug assembly 204. The housing assembly 202 is configured to be securely mounted within the reload assembly 16 (FIG. 4), and the plug assembly 204 is configured to be securely mounted within a distal end 14b of the adapter assembly 14 (FIG. 1).

Figure 14:
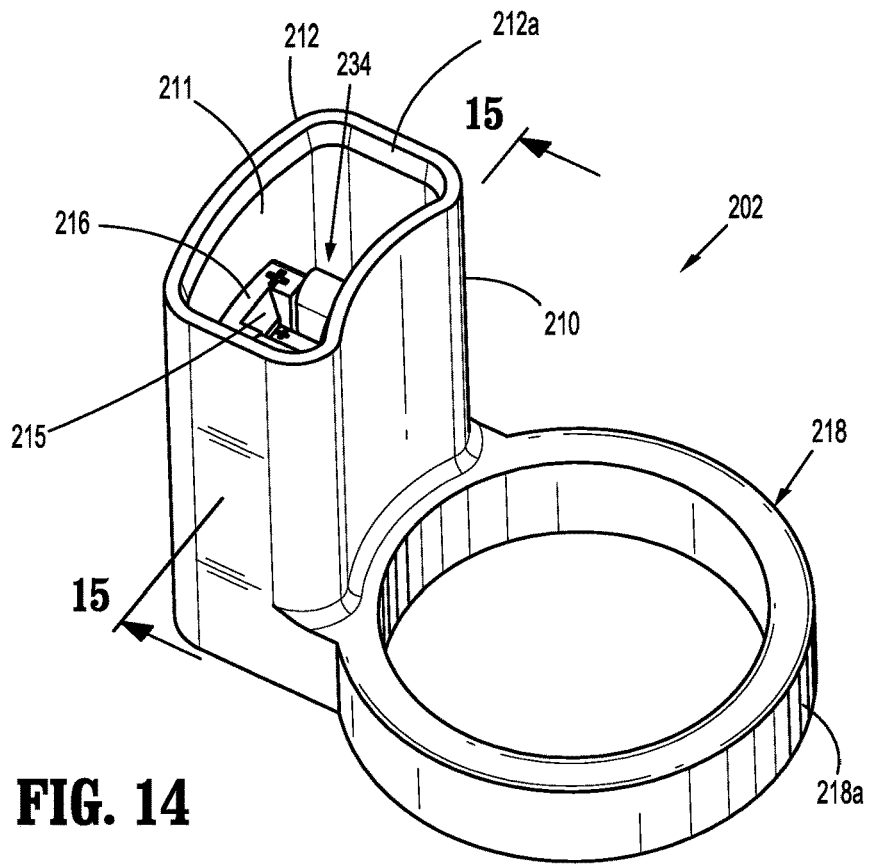
FIG. 14 is a perspective view of the housing assembly of the chip assembly shown in FIGS. 12 and 13.
Figure 15:
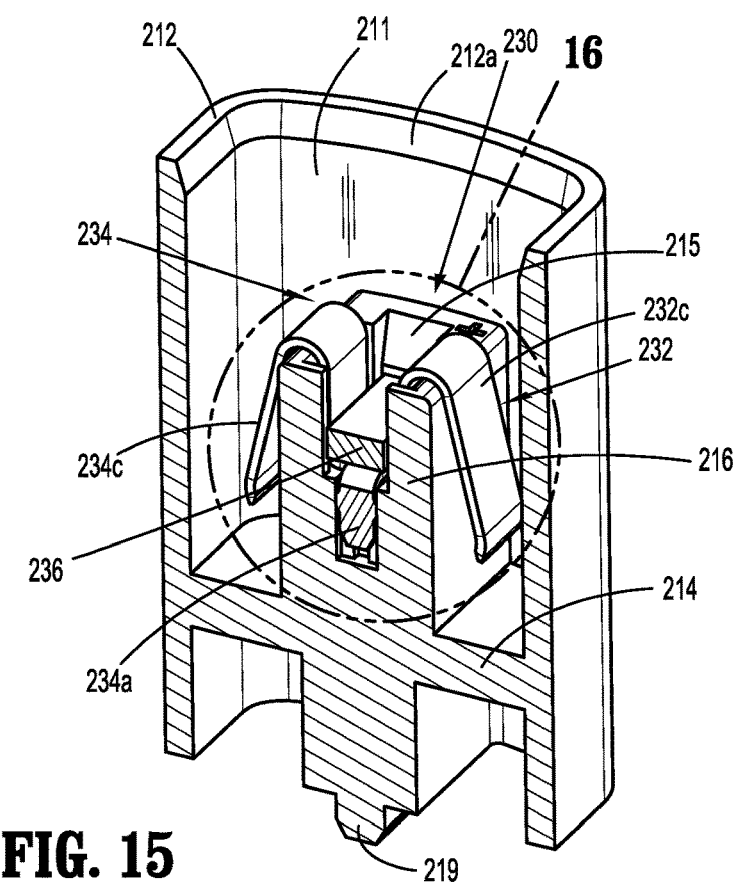
FIG. 15 is a cross-sectional side view taken along line 15-15 shown in FIG. 14.
Figure 16:
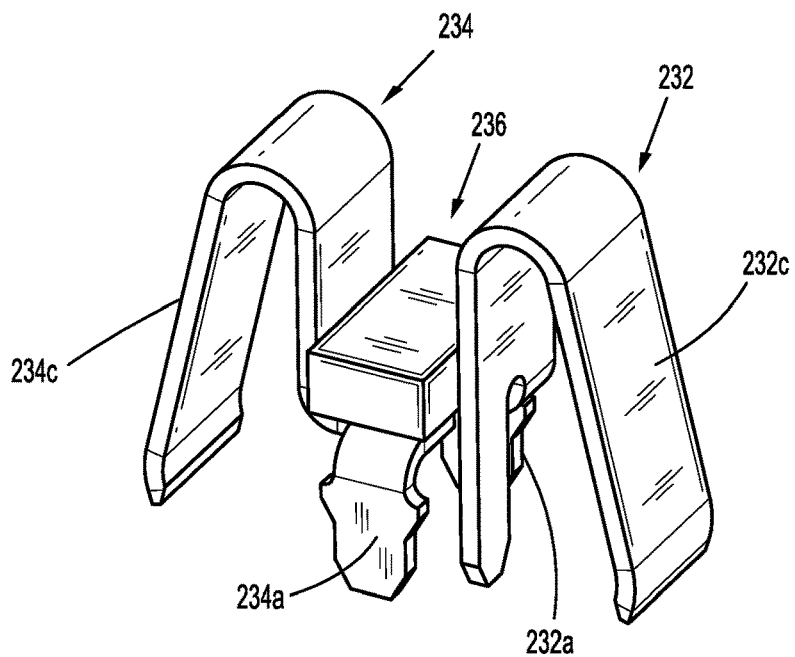
FIG. 16 is an enlarged view of the indicated area of detail shown in FIG. 15, including an identification assembly.
Figure 17:
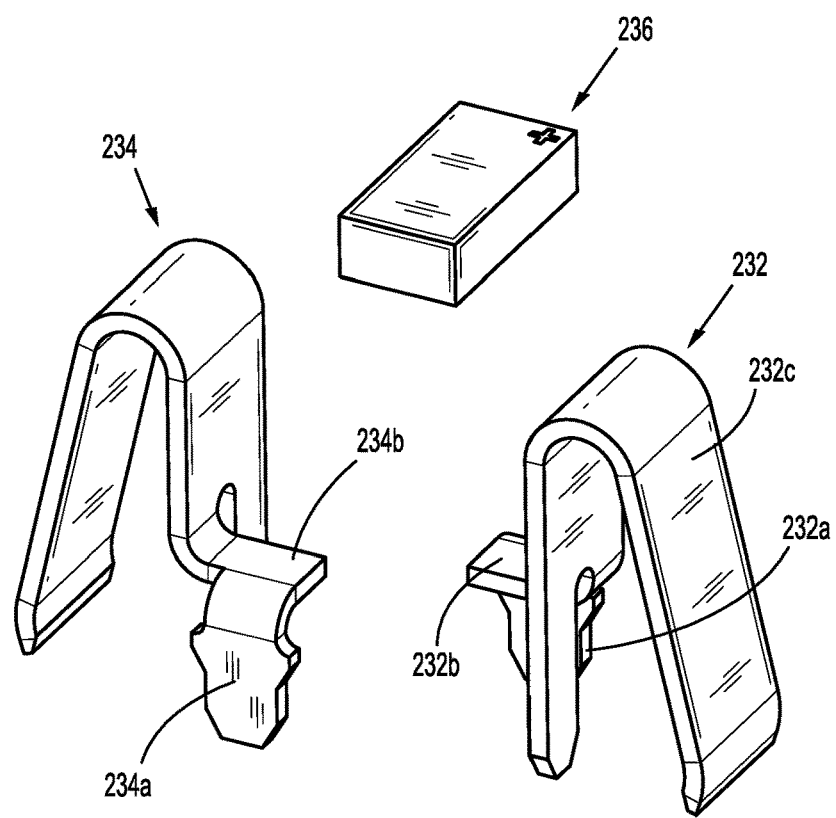
FIG. 17 is a perspective view of the identification assembly shown in FIG. 16, illustrating first and second contact members and a chip thereof separated.

With particular reference to FIGS. 14 and 15, the housing assembly 202 includes a base member or housing 210 defining a cavity 211 and including an open first end 212 and a closed second end 214. The open first end 212 of the base member 210 includes a tapered surface 212a. As will be described in further detail below, the tapered surface 212a of the base member 210 facilitates engagement of the plug assembly 204 (FIG. 12) of the chip assembly 200 (FIG. 12) with the housing assembly 202. It is envisioned that the base member 210 is one piece, e.g., monolithic, to ensure that the cavity 211 is fluid tight. However, the base member 210 may be formed as two or more components that are joined together in a fluid tight manner, e.g., welding, adhesive.

With continued reference to FIG. 15, the base member 210 of the housing assembly 202 includes a support portion 216 extending from the closed second end 214 of the base member 210. The support portion 216 is configured to support identification assembly 230. More particularly, the support portion 216 defines a recess 215 configured to receive the identification assembly 230. The support portion 216 and the base member 210 may be integrally formed, e.g., monolithic, or may be secured to one another using any suitable technique.

The base member 210 of the housing assembly 202 of the chip assembly 200 further includes a connection member 218 for securing the housing assembly 202 within reload assembly 16 (FIG. 2). As shown, the connection member 218 includes an annular flange 218a extending perpendicular to a longitudinal axis "y" (FIG. 23) of base member 210. The annular flange 218a is configured to be received about a tubular sleeve 22 (FIG. 4) of reload assembly 16 (FIG. 1). In embodiments, the connection member 218 may include a C-clip, a clamp, a bracket, or any other suitable mechanism.

In embodiments, and as shown, the base member 210 further includes one or more alignment features 219 (FIG. 10). The alignment feature 219 forms a protrusion extending outwardly from the closed second end 214 of the base member 210. The alignment feature 219 facilitates alignment of the base member 210 within the reload assembly 16 and/or prevents rotational movement of the housing assembly 202 during transport, loading, and use of the reload assembly 16.

The identification assembly 230 includes first and second contact members 232, 234, and a chip 236 extending between the first and second contact members 232, 234. The first and second contact members 232, 234 each include an anchor portion 232a, 234a, respectively, for securing the identification assembly 230 to the support portion 216, a connector portion 232b, 234b, respectively, for connecting each of the first and second contact members 232, 234 to the chip 236, and a leaf spring portion 232c, 234c for engaging first and second contact members 242, 244 of a connector assembly 240 of the plug assembly 204.

The chip 236 of the identification assembly 230 may include any commercially available chip capable of storing the specifications of the reload assembly 16, e.g., cartridge size, staple arrangement, staple length, clamp-up distance, etc., and transmitting the specifications to the handle assembly 12 (FIG. 1). In embodiments, the chip 236 includes a 1-Wire Chip, e.g., provides low-speed data, signaling, and power over a single conductor. By utilizing a 1-Wire Chip, the identification assembly does not need a printed circuit board. This simplifies the manufacturing process and/or lowers the costs of the chip assembly 200.

Figure 18:
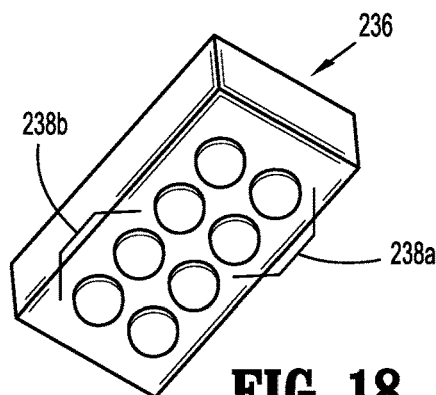
FIG. 18 is a perspective view of the chip of the identification assembly shown in FIGS. 16 and 17.
Figure 19:
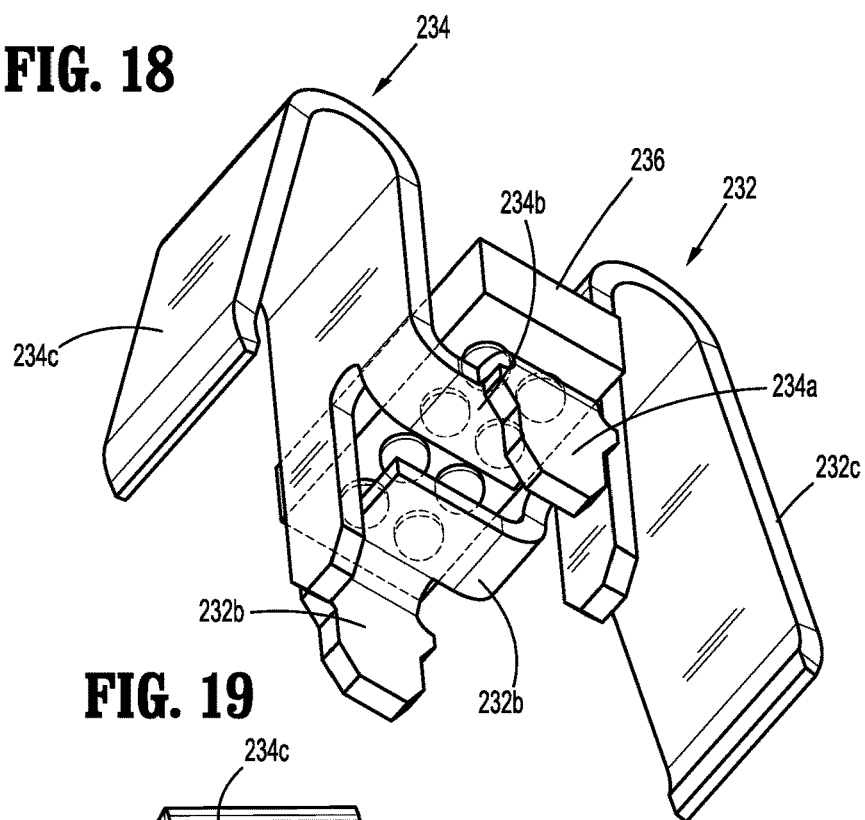
FIG. 19 is a perspective bottom view of the identification assembly shown in FIGS. 16 and 17.
Figure 20:
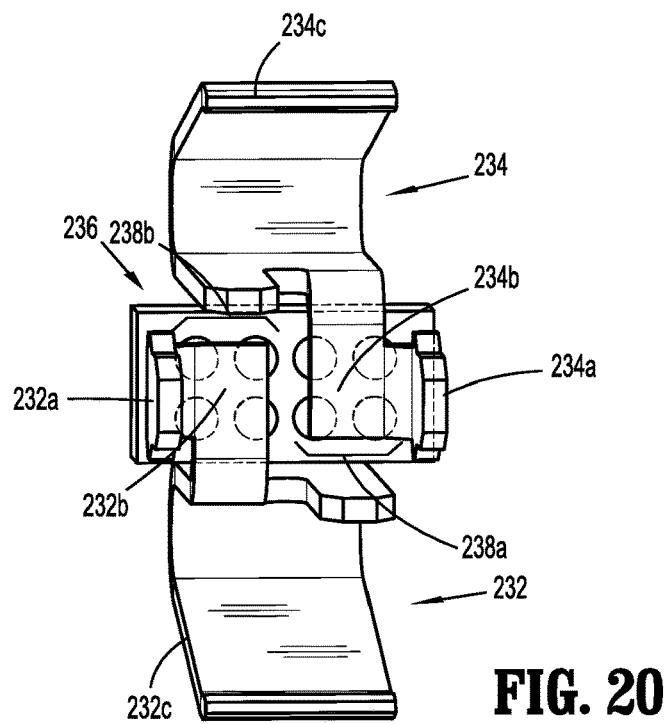
FIG. 20 is a bottom view of the identification assembly shown in FIG. 19.

As shown in FIGS. 18 and 19, the chip 236 includes a first and second plurality of contacts 238a, 238b. The first plurality of contacts 238a is electrically coupled to the connector portion 232b of the first contact member 232, and the second plurality of contacts 238b is electrically coupled to the connector portion 234b of the second contact member 234. Although shown as including two plurality of contacts 238a, 238b, it is envisioned that the chip 236 may include only a single contact for electrical coupling each of the respective first and second contact members 232, 234 with the chip 236. In embodiments, the chip 236 includes a 1-Wire Chip that is placed directly onto the first and second contact members 232, 234, and is secured in place using known techniques, e.g., re-flow soldering.

The chip 236 of the identification assembly 230 may be secured to the first and second contact members 232, 234 of the housing assembly 202 prior to or after the first and second contact members 232, 234 are secured to the support portion 216 of the base member 210. Once the chip 236 is secured to the first and second contact members 232, 234, the identification assembly 230 may then be press-fit within the recess 215 of the support portion 216 of the base member 210. Alternatively, the first and second contact members 232, 234 may first be press-fit within the recess 215 of the support portion 216 of the base member 210. The chip 236 may then be secured to the first and second contact members 232, 234, as described above, and/or the chip 236 may be press-fit within the recess 215 of the support portion 216 of the base member 210.

The first and second contact members 232, 234 of the identification assembly 230 are configured such that when the first and second contact members 232, 234 are secured to the support portion 216 of the base member 210, the leaf portions 232c, 234c of the respective first and second contact members 232, 234 extend outwardly from the support portion 216 of the base member 210 an amount sufficient to ensure contact between the first and second contact members 232, 234 and the respective first and second contact members of 262, 264 of the plug assembly 204.

Figure 22:
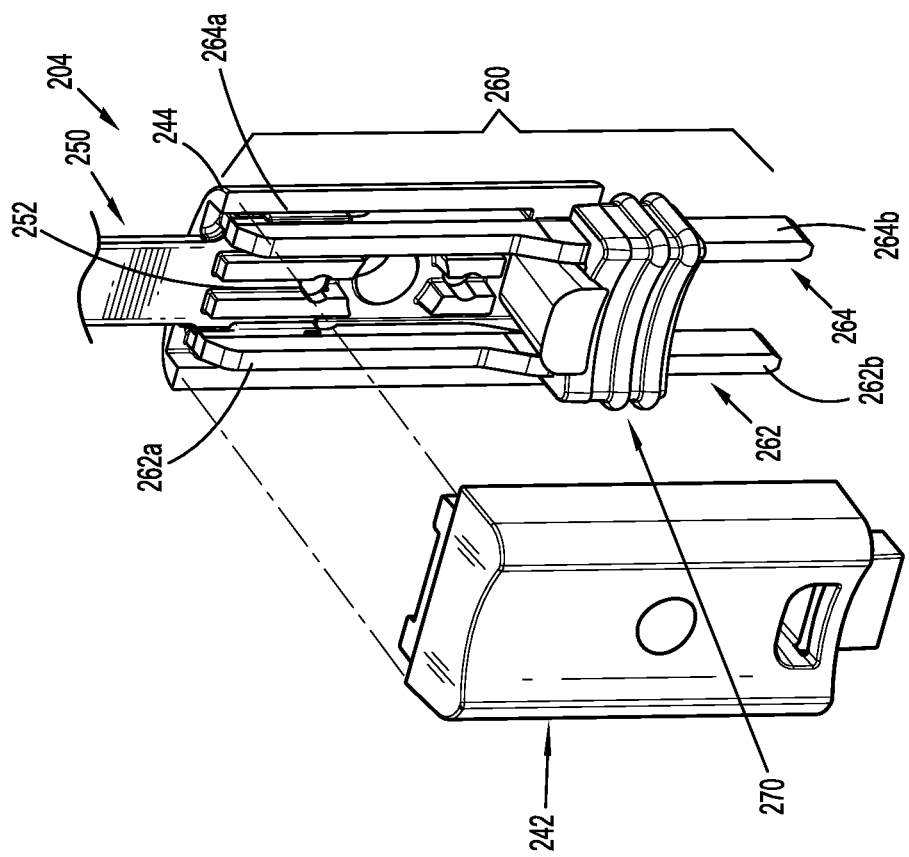
FIG. 22 is a perspective view of the plug assembly shown in FIG. 12, with a cover member removed.
Figure 21:
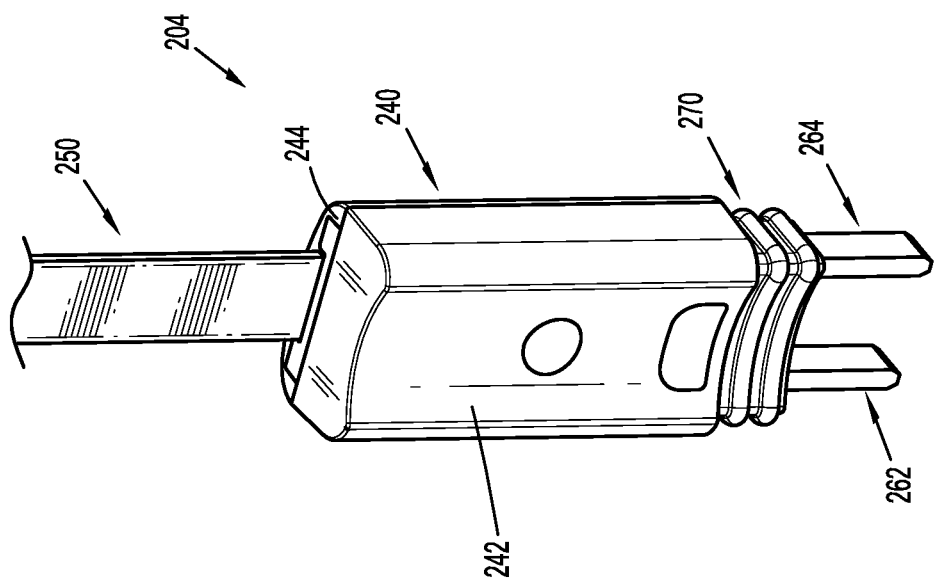
FIG. 21 is a perspective view of a plug assembly of the chip assembly shown in FIG. 12.
Figure 24:
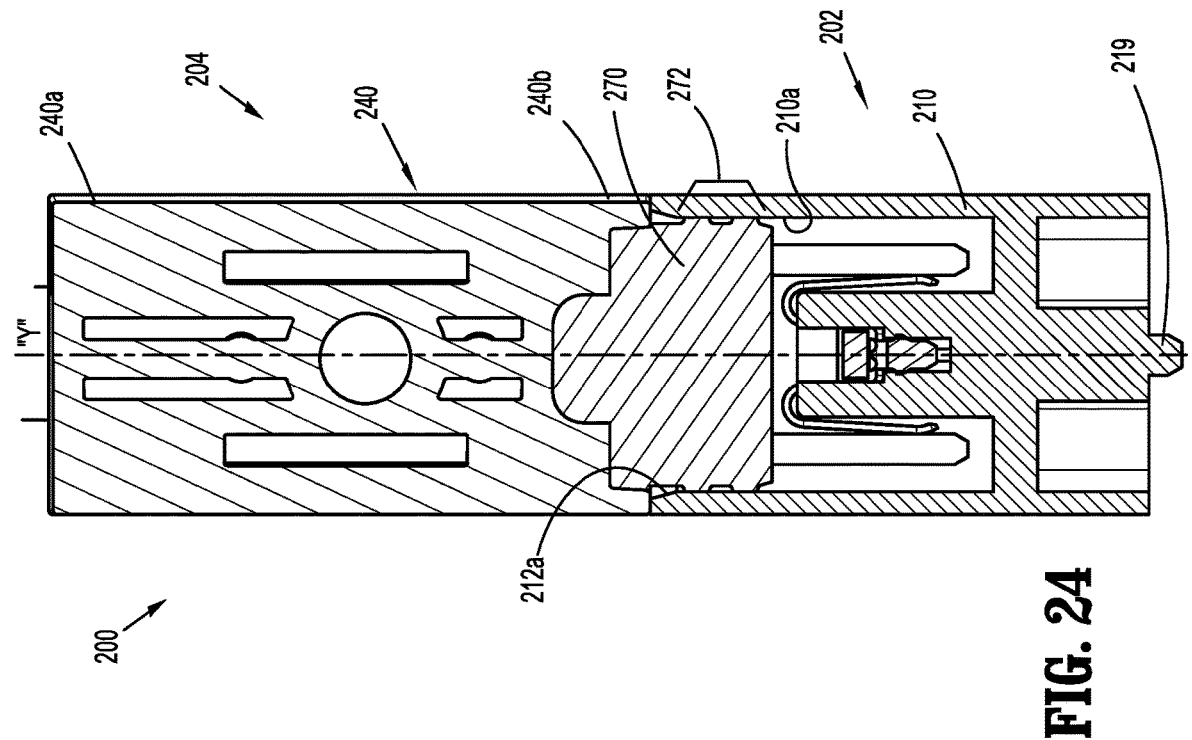
FIG. 24 is a cross-sectional side view taken along line 24-24 shown in FIG. 23.
Figure 23:
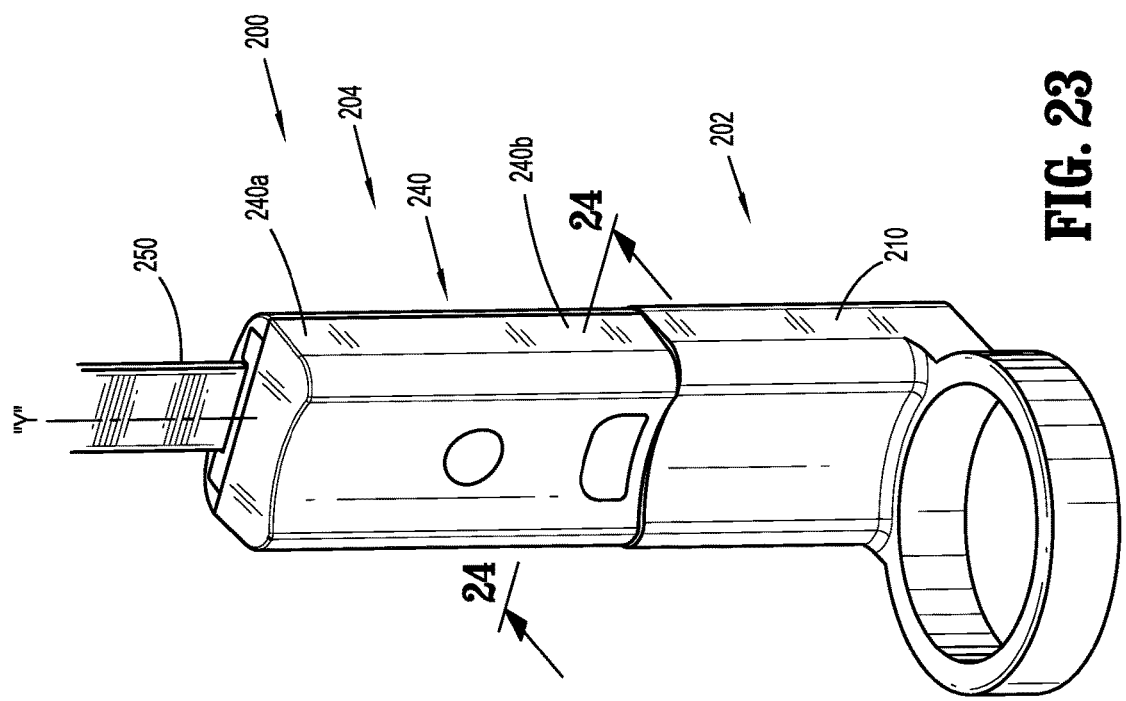
FIG. 23 is a perspective view of the chip assembly shown in FIG. 12 with the plug assembly secured to the housing assembly.

With reference to FIGS. 21 and 22, the plug assembly 204 of the chip assembly 200 includes a housing 240, an electrical ribbon or wire 250 extending from a proximal end 240a of the housing 240, and a connector assembly 260 disposed within and extending from a distal end 240b of the housing 240. The plug assembly 204 is configured to electrically couple the chip 236 of the identification assembly 230 of the housing assembly 202 with the handle assembly 12.

In embodiments, and as shown, the housing 240 of the plug assembly 204 includes first and second half sections 242, 244 configured to receive a distal end 250b of the electrical ribbon 250, and the connector assembly 260 in a fluid tight manner. The first and second half sections 242, 244 of the housing 240 may be secured together in any suitable manner, e.g., welded, a snap fit connection, adhesive, overmolded, coated, potted. It is envisioned that the first and second half sections 242, 244 may be releasably secured to one another to permit removal and replacement of the connector assembly 260. In embodiments, housing 240 may instead be molded about the distal end 250b of the electrical ribbon 250 and the connector assembly 260 to form a one-piece, fluid-tight housing (not shown).

With continued reference to FIG. 22, the connector assembly 260 of the plug assembly 204 includes first and second contact members 262, 264 in electrical communication with the electrical ribbon 250, and a seal member 270 disposed on distal end of the housing 240. In particular, proximal end 262a, 264a of the first and second contact members 262, 264 are electrically coupled with and secured to and/or secured relative to the distal end 252 of the electrical ribbon 250.

The seal member 270 of the connector assembly 260 of the plug assembly 204 is secured to and extends from a distal end of the housing 240. The seal member 270 is configured to be received through the open first end 212 of the base member 210 of the housing assembly 202 and form a friction fit. As noted above, the open first end 212 of the base member 210 may include a tapered surface 212a (as shown), to facilitate receipt of the seal assembly 270 within the cavity 211 of the base member 210. The seal member 270 may include ridges 272 configured to engage an inner wall 210a of the base member 210 of the housing assembly 202 to facilitate the friction fit between the base member 210 of the housing assembly 202 and the seal member 270 of the plug assembly 204. The seal member 270 is configured to create a fluid tight seal between the housing assembly 202 and the plug assembly 204 when the housing assembly 202 is releasably secured to the plug assembly 204. The seal member 270 may be formed of rubber, plastic, polymer, or any other suitable material.

The distal ends 262b, 264b of the first and second contact members 262, 264, respectively, of the connector assembly 260 of the plug assembly 204, extend through and from the seal member 270. The distal ends 262b, 264b of the first and second contact members 262, 264 are configured to electrically couple with the respective leaf spring portions 232c, 234c of the respective first and second contact members 232, 234 of the identification assembly 230 of the housing assembly 202 when the housing assembly 202 is coupled with the plug assembly 204.

The operation of the chip assembly 200 is substantially similar to the operation of chip assembly 100 described hereinabove. The housing assembly 202 is disposed within the reload assembly 16 (FIG. 1) and the plug assembly 204 of the chip assembly 200 is disposed within the adapter assembly 14 (FIG. 1) such that when the reload assembly 16 is secured to the adapter assembly 14, the housing assembly 202 engages the plug assembly 204. Specifically, when the reload assembly 16 is secured to the adapter assembly 14, the first and second contact members 262, 264 and the seal member 270 of the connector assembly 260 are received through the open first end 212 of the base member 210 of the housing assembly 202 and into the cavity 211 of the base member 210. As noted above, the tapered surface 212a of the open first end 212 of the base member 210 facilitates receipt of the seal member 270 within the cavity 211. The ridges 272 of the seal member 270 frictionally engage the inner walls 210a of the base member 210 to frictionally secure the plug assembly 204 to the housing assembly 202 and create a fluid tight seal between the plug assembly 204 and the housing assembly 202.

As the first and second contact members 262, 264 of the plug assembly 204 are received within the cavity 211 of the base member 210 of the housing assembly 202, the first and second contact members 262, 264 engage the respective leaf spring portions 232c, 234c of the respective first and second contact members 232, 234 of the identification assembly 230 of the housing assembly 202. The outward extension of the leaf spring portions 232c, 234c of the receptive first and second contact members 232, 234 ensures contact between the distal ends 232b, 234b of the first and second contact members 232, 234 of the identification assembly 230 of the housing assembly 202 and the first and second contact members 262, 264 of the connector assembly 260 of the plug assembly.

Once the reload assembly 16 is properly secured to the adapter assembly 14, and thus, the housing assembly 202 of the chip assembly 200 is electrically coupled with and secured to the plug assembly 204 of the chip assembly 200, the circular stapler is ready for use.

Figure 27:
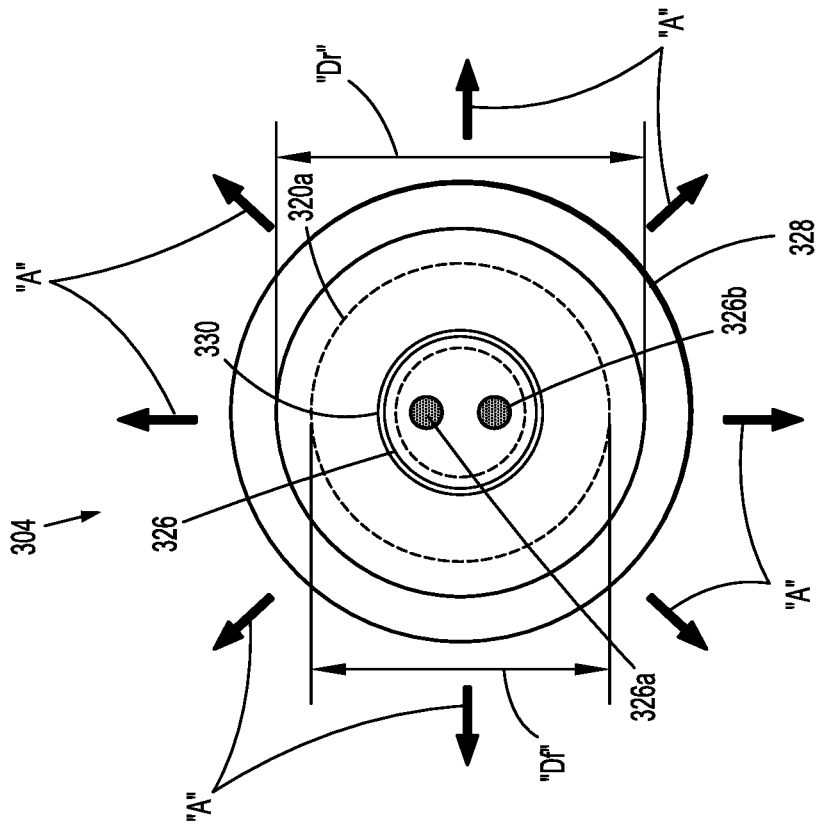
FIG. 27 is an end view of the plug assembly shown in FIG. 25.
Figure 26:
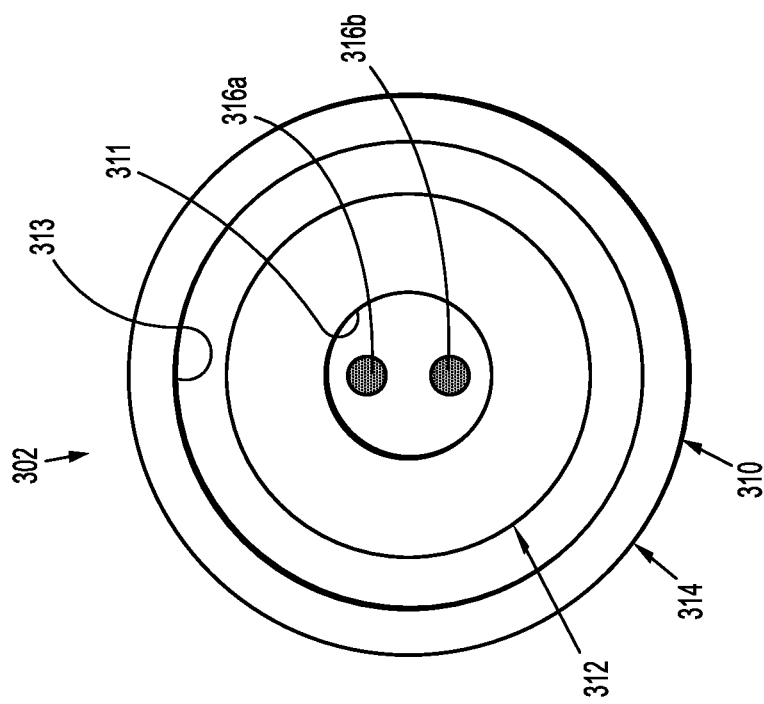
FIG. 26 is an end view of the housing assembly shown in FIG. 25.

With reference now to FIGS. 25-27, a chip assembly including a floating connection is shown generally as chip assembly 300. The chip assembly 300 is substantially similar to the chip assemblies 100 and 200 described hereinabove, and will only be described in detail as relates to the differences therebetween. The chip assembly 300 includes a housing assembly 302, and a plug assembly 304. The housing assembly 302 is configured to be securely mounted within a reload assembly 16 (FIG. 4), and the plug assembly 304 is configured to be securely mounted within a distal end 14b (FIG. 1) of the adapter assembly 14 (FIG. 1). Although shown and described with the floating connection formed on the plug assembly 304, it is envisioned that either or both of the housing assembly 302 and the plug assembly 304 may include a floating connection.

With particular reference to FIGS. 25 and 26, the housing assembly 302 of the chip assembly 300 includes a base member or housing 310. The base member 310 includes an inner annular flange 312 and an outer annular flange 314. The inner annular flange 312 of the base member 310 defines an inner cavity 311. An annular cavity 313 is defined between the inner annular flange 312 and the outer annular flange 314. Each of the inner and outer flanges 312, 314 include a tapered free end 312a, 314b configured to facilitate alignment of the housing assembly 302 with the plug assembly 304.

The housing assembly 302 of the chip assembly 300 includes first and second contact members 316a, 316b extending from the base member 310 into the inner cavity 311 defined by the inner annular flange 312. The first and second contact members 316a, 316b and are configured to engage respective first and second contact members 326a, 326b of the plug assembly 304 when the plug assembly 304 is secured to the housing assembly 302. Biasing members, e.g., springs 315a, 315b, bias respective first and second contact members 316a, 316b outwardly to facilitate engagement with the respective first and second contact members 316a, 316b of the plug assembly 304.

With particular reference now to FIGS. 25 and 27, the plug assembly 304 of the chip assembly 300 includes a fixed base 320 and a floating housing 322 supported on the fixed base 320. More particularly, the floating housing 322 defines a recess 321 and the fixed base 320 includes a flange 320a that is received within the recess 323. A diameter "Df" of the flange 324 is smaller than a diameter "Dr" of the recess 323 to permit planar movement of the floating housing 322 relative to the fixed base 320, as indicated by arrows "A" in FIG. 27. A biasing member (not shown), for example, a viscoelastic material (not shown), may be received about the flange 320a of the fixed base 320 and within the recess 323 of the floating housing 322 to maintain the floating housing 322 in axial alignment with the fixed base 320 prior to the plug assembly 304 being secured to the housing assembly 302, and permit movement of the floating housing 322 to facilitate securing the plug assembly 304 to the housing assembly 302.

With continued reference to FIGS. 25 and 27, the floating housing 322 of the plug assembly 304 of the chip assembly 300 includes plug member 326 extending distally therefrom. The plug member 326 includes first and second contact members 326a, 326b disposed on the free end thereof. The plug member 326 is configured to be received within the inner cavity 311 of the base member 310 of the housing assembly 302. The first and second contact members 326a, 326b are configured to engage the first and second contact members 316a, 316b of the housing assembly 302 when the plug assembly 304 is secured to the housing assembly 302.

The floating housing 322 further includes an annular flange 328 disposed about the plug member 326. The annular flange 328 includes a tapered free end 328a configured to facilitate receipt of the annular flange 328 within the annular cavity 313 formed between the inner annular flange 312 and the outer annular flange 314.

A seal member 330 is received about the plug member 326, and is configured to create a seal between the plug member 326 of the plug assembly 304 and the inner annular flange 312 of the housing assembly 302.

The operation of the chip assembly 300 is substantially similar to the operation of chip assemblies 100 and 200 described hereinabove. The housing assembly 302 of the chip assembly 300 is disposed within the reload assembly 16 (FIG. 1) and the plug assembly 304 of the chip assembly 300 is disposed within the adapter assembly 14 (FIG. 1) such that when the reload assembly 16 is secured to the adapter assembly 14, the housing assembly 302 engages the plug assembly 304. Specifically, when the reload assembly 16 is secured to the adapter assembly 14, the plug member 326 of the plug assembly 302 is received within the cavity 311 of the housing assembly 302. Receipt of the plug member 326 of the plug assembly 302 within the cavity 311 of the housing assembly 302 is facilitated by engagement of the tapered free end 312a of inner annular flange 312 of the housing assembly 302 with the plug member 326 and of the tapered free end 314a of the outer annular flange 314 of the plug assembly 302.

As described in detail above, the floating housing 322 of the plug assembly 304 is configured to permit planar movement of the floating housing 322 relative to the fixed base 320 of the plug assembly 304 to facilitate alignment of the plug member 326 of the plug assembly 304 with the cavity 311 of the housing assembly 302. When the plug member 326 of the plug assembly 304 is properly received within the cavity 311 of the housing assembly 302, the first and second contact members 316a, 316b of the housing assembly 302 engage respective corresponding first and second contact members 326a, 326b of the plug assembly 304. As noted above, the first and second contact members 316a, 316b of the housing assembly 302 are biased outwardly by springs 315a, 315b (FIG. 25) to facilitate engagement between the first contact members 316a, 326a and between the second contact members 326a, 326b.

With reference now to FIG. 28, an alternative embodiment of a chip assembly including a floating connection is shown generally as chip assembly 400. The chip assembly 400 is substantially similar to chip assemblies 100, 200, and 300 described hereinabove, and will only be described in detail as relates to the differences therebetween. The chip assembly 400 includes a housing assembly 402 and a plug assembly 404. Although shown with the floating connection being include in the plug assembly 404, it is envisioned that either or both of the housing assembly 402 and the plug assembly 404 may including a floating connection to facilitate alignment of the housing assembly 402 and the plug assembly 404.

Briefly, the housing assembly 402 includes a base member 410 defining a cavity 411. First and second contact members 416a, 416b extend into the cavity 411 and are configured to engage a plug member 426 of the plug assembly 404 when the plug member 426 is received within the cavity 411. It is envisioned that the base member 410 may include other configurations.

With reference now to FIGS. 29 and 30, the plug assembly 404 of the chip assembly 400 includes a fixed base 420 and a floating housing 422. With initial reference to FIG. 29, the fixed base 420 is includes first and second pins 420a, 420b for securing the floating housing 422 to the fixed bases 420. The first and second pins 420a, 420b may also provide electrical contact between the fixed base 420 and the floating housing 422.

Turning now to FIG. 30, the floating housing 422 of the plug assembly 404 includes the plug member 426 and a seal 430 supported on the plug member 426. The floating housing 422 defines a cavity 423 for receipt of the fixed base 420, a first opening 423a for receipt of the first pin 420a of the fixed base 420 and a second opening 423b for receipt of the second pin 420b of the fixed base 420. As shown the second opening 423b is in the form of a semi-circle or arc.

Figure 31:
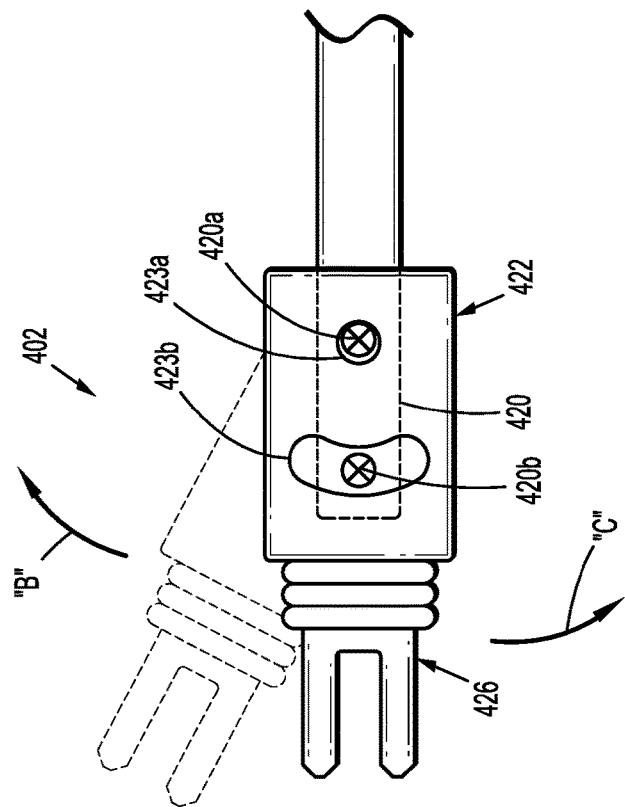
FIG. 31 is a side view of the plug assembly shown in FIG. 28.

With particular reference now to FIG. 31, the first pin 420a of the fixed base 420 acts a pivot about with the floating housing 422 may pivot relative to the fixed base 420, as indicated by arrows "B" and "C". The second pin 420b of the fixed base 420 and the second opening 423b of the floating housing 422 operate to limit the pivoting of the floating housing 422 relative to the fixed base 420.

Figure 32:
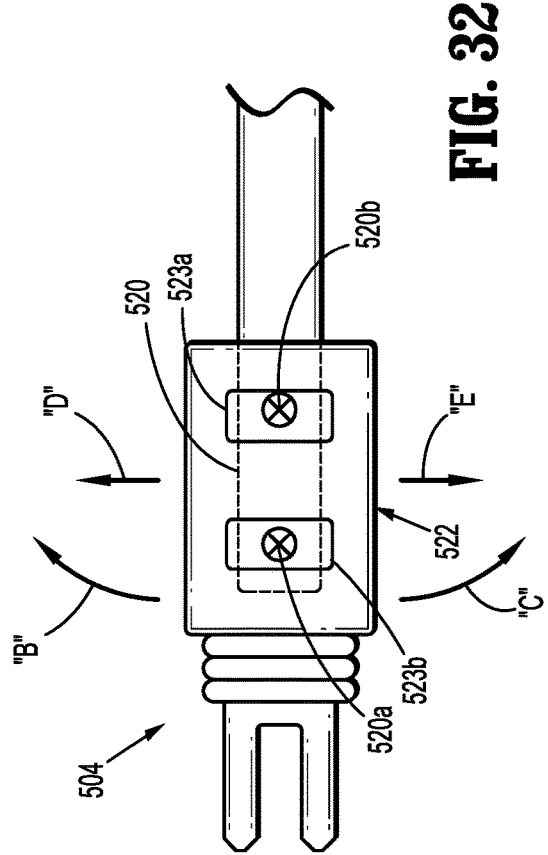
FIG. 32 is a side view of an alternative embodiment of the plug assembly shown in FIG. 28.

With reference now to FIG. 32, in another embodiment of a chip assembly, a floating housing 522 of a plug assembly 504 includes first and second openings 523a, 523b. The first and second openings 523a, 523b are configured to receive respective first and second pins 520a, 520b of the fixed base 520. The first and second openings 523a, 523b are oversized opening that permit both rotational movement, as indicated by arrows "B" and "C", and lateral movement, as indicated by arrows "D" and "E", of the of the floating housing 522 relative to the fixed base 520.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A chip assembly for use in a surgical stapler, the chip assembly comprising:
   a housing assembly including a base member defining a cavity and an identification assembly received within the cavity; and
   a plug assembly configured to selectively engage the base member of the housing assembly, the plug assembly including a housing, a wire extending from the housing, a seal member disposed within and extending from a distal end of the housing, and first and second contact members extending through the seal member and from the housing, wherein the seal member is configured to be frictionally received within the base member to secure the plug assembly to the housing assembly in a fluid tight manner.

2. The chip assembly of claim 1, wherein the identification assembly includes first and second contact members and a chip.

3. The chip assembly of claim 2, wherein the chip is a 1-Wire Chip.

4. The chip assembly of claim 3, wherein the chip is secured directly to the first and second contact members.

5. The chip assembly of claim 3, wherein the chip is soldered directly to the first and second contact members.

6. The chip assembly of claim 3, wherein the chip is an EPROM chip.

7. The chip assembly of claim 2, wherein the first and second contact members of the plug assembly are configured to engage the chip when the plug assembly engages the housing assembly.

8. The chip assembly of claim 1, wherein the housing assembly further includes first and second contact members configured to selectively engage the respective first and second contact members of the plug assembly when the plug assembly is engaged with the base member of the housing assembly.

9. The chip assembly of claim 1, wherein the housing includes first and second half sections.

10. The chip assembly of claim 1, wherein the base member includes an open end having a tapered surface configured to facilitate receipt of the seal member within the base member.

11. The chip assembly of claim 1, wherein the seal member includes a plurality of ridges configured to facilitate a friction fit between the housing assembly and the plug assembly.

12. A surgical stapling device comprising:
a handle assembly;
an adapter assembly extending from the handle assembly;
a reload assembly operably connected to a distal end of the adapted assembly; and
a chip assembly including a housing assembly and a plug assembly, the housing assembly receivable within the reload assembly, the housing assembly including a base member and an identification assembly, the identification assembly including first and second contact members and a 1-Wire Chip secured directly to the first and second contact members, the plug assembly including a housing and a seal member disposed within and extending from a distal end of the housing, the seal member configured to selectively engage the base member in a fluid tight manner when the plug assembly is in engagement with the housing assembly.

13. A chip assembly for use in a surgical stapler, the chip assembly comprising:
a housing assembly including a base member defining a cavity and an identification assembly received within the cavity; and
a plug assembly configured to selectively engage the base member of the housing assembly, the plug assembly including a fixed base and a floating housing movably secured to the fixed base to facilitate engagement between the floating housing and the identification assembly.

* * * * *